US007897790B2

(12) United States Patent
Katsumura et al.

(10) Patent No.: US 7,897,790 B2
(45) Date of Patent: Mar. 1, 2011

(54) THIOPHENE COMPOUND AND PROCESS FOR PRODUCING CAFFENOFURAN OR ANALOGUE THEREOF FROM THE SAME

(75) Inventors: Shigeo Katsumura, Sanda (JP); Yanwu Li, Sanda (JP); Hisakatsu Iwabuchi, Toyonaka (JP); Masanobu Onishi, Toyonaka (JP); Yusuke Murakami, Toyonaka (JP)

(73) Assignee: San-Ei Gen F.F.I., Inc., Osaka (JP)

( * ) Notice: Subject to any disclaimer, the term of this patent is extended or adjusted under 35 U.S.C. 154(b) by 822 days.

(21) Appl. No.: 11/884,737

(22) PCT Filed: Feb. 22, 2006

(86) PCT No.: PCT/JP2006/303122

§ 371 (c)(1),
(2), (4) Date: Aug. 21, 2007

(87) PCT Pub. No.: WO2006/090716

PCT Pub. Date: Aug. 31, 2006

(65) Prior Publication Data

US 2008/0167481 A1 Jul. 10, 2008

(30) Foreign Application Priority Data

Feb. 22, 2005 (JP) .............................. 2005-045014

(51) Int. Cl.
C07D 495/06 (2006.01)
(52) U.S. Cl. ...................................................... 549/50
(58) Field of Classification Search .................... 549/50
See application file for complete search history.

(56) References Cited

U.S. PATENT DOCUMENTS

| 3,652,593 A | 3/1972 | Gautschi et al. |
| 3,753,738 A | 8/1973 | Gautschi et al. |

FOREIGN PATENT DOCUMENTS

| JP | 48-14067 A | 5/1973 |
| JP | S 48-14067 B | 5/1973 |
| JP | 2003-212867 A | 7/2003 |
| WO | WO 2004-031109 A2 | 4/2004 |
| WO | WO 2004/031109 A2 | 4/2004 |

OTHER PUBLICATIONS

European Search Report dated Jan. 4, 2010.
Iriye, Ryozo et al., "The Formation of Alkylfurans from (E)-4-Hydroxy-2-alkenals and (E)-4-Oxo-2-atkenols, and a synthesis of Rosefuran," Agric. Biol. Chem., vol. 54, No. 7, pp. 1841-1843, 1990.
Li, Yanwu, et al., "Rapid synthesis of kahweofuran and its derivatives, the coffee aroma components," Elsevier, Tetrahedron Letters, vol. 47, pp. 787-789, 2006.
Itaru Sato et al., Heterocycles, vol. 51, No. 11, 1999, pp. 2753-2758; *1-Phenyl-2-(1-Pyrrolidinyl)-1-Propanol as a Chiral Catalyst for the Highly Enantioselective Addition of Dialkylzincs to Five-Membered Heterocyclic Aldehydes.*
Judy M. Holmes et al., Journal of Medical Chem, 1994, vol. 37, pp. 1646-1651, *Synthesis and Carbonic Anhydrase Inhibitory Activity of 4-Substituted 2-Thiophenesulfonamides.*
Peter N. Nugara et al., Sulfur Letters, vol. 14(6), pp. 269-273, 1992; *Convenient Reduction of Thienyl Alcohols.*
S. Gronowitz et al., Journal of the Chemical Society, 1963, pp. 3881-3882; *Infrared Absorption of Heteroaromatic, Five-membered, Monocyclic Nuclei. Part IV. 3-Monosubstituted Thiophens.*
Roland Tressl et al., Journal of Agricultural and Food Chemistry, 1981, vol. 29, No. 5, pp. 1078-1082; *Investigation of Sulfur-Containing Components in Roasted Coffee.*
R. Liardon et al., Lebensmittel-Wissenschaft und-Technologie, 1984, vol. 17, No. 1, pp. 32-28; *Application of Multivariate Statistics for the Classification of Coffee Headspace Profiles.*

(Continued)

Primary Examiner—Taofiq A Solola
(74) Attorney, Agent, or Firm—Fitch, Even, Tabin & Flannery

(57) ABSTRACT

The present invention provides a novel thiophene compound as a synthetic intermediate that is useful for efficient production of kahweofuran or an analogue thereof. The present invention also provides a process for producing kahweofuran or an analogue thereof using the novel thiophene compound as an intermediate material.

Of novel thiophene compounds represented by Formula (1):

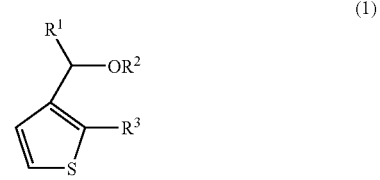

(1)

wherein $R^1$ is a hydrogen atom or a $C_1$-$C_4$ lower alkyl group; $R^2$ is a hydrogen atom or an alcohol-protecting group; $R^3$ is a hydrogen atom, —$COR^4$ or —$C(OH)R^5$ (wherein $R^4$ and $R^5$ each represent a $C_1$-$C_4$ lower alkyl group); provided that when $R^2$ and $R^3$ are hydrogen atoms, $R^1$ is not any of a hydrogen atom, methyl group, or n-propyl group; a thiophene compound represented by Formula (2) is reduced and cyclized in the presence of a transition metal catalyst to produce kahweofuran or kahweofuran analogue (3a) shown below:

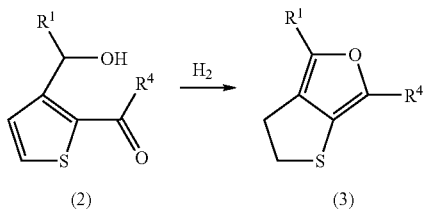

(2) (3)

wherein $R^1$ is a hydrogen atom or a $C_1$-$C_4$ lower alkyl group, and $R^4$ is a $C_1$-$C_4$ lower alkyl group.

11 Claims, No Drawings

OTHER PUBLICATIONS

J. Org. Chem., Vo. 36, No. 1, pp. 199-200; 1971; *Structure and Synthesis of Kahweofuran, a Constituent of Coffee Aroma*.

J. Chem. Research (S), 1998, pp. 74-75; *Synthesis of 2, 3-Dihydro-6-methylthieno[2,3-c] Furan (Kahweofuran), a Coffee Aroma Component, from an Acyclic Precursor*.

E. Brenna et al., Paper E/7/06334B Received Aug. 29, 1997; pp. 551-563; *Synthesis of 2, 3-Dihydro-6-Methylthieno[2, 3-c] Furan (Kahweofuran), a Coffee Aroma Component, from an Acyclic Precursor*.

Marek Gorzynski et al., Liebigs Ann. Chem., 1986, pp. 625-637; *Synthese von Alkyl-2, 3-dihydrothieno[2,3-c]furanen, Aromastoffen des Kaffees*.

Helvetica Chimica Acta, 50, pp. 628-694, 1967; *68. Recherches sur les aromes*.

THIOPHENE COMPOUND AND PROCESS FOR PRODUCING CAFFENOFURAN OR ANALOGUE THEREOF FROM THE SAME

This Application is the U.S. National Stage Application under 35 U.S.C. 371 of PCT International Application PCT/JP2006/303122 filed Feb. 22, 2006, which claims benefit from Japanese Patent Application No. 2005-45014 filed Feb. 22, 2005, the complete disclosures of which are incorporated herein by reference.

TECHNICAL FIELD

The present invention relates to a novel thiophene compound. The present invention also relates to a process for producing kahweofuran or an analogue thereof (hereinafter each referred to as a "kahweofuran compound") using the novel thiophene compound as an intermediate material. The novel thiophene compound of the present invention is useful as a synthetic intermediate for a kahweofuran compound, which is an aroma component. The present invention further relates to a novel thiophene compound that itself has an aroma and can be effectively used as an aroma component (hereafter this compound is referred to as "aromatic thiophene compound" to distinguish it from the above-mentioned thiophene compound).

BACKGROUND ART

Kahweofuran (compound name: 2,3-dihydro-6-methylthieno[2,3-c]furan) is a compound that was isolated by M. Stoll et al. in 1963 as a characteristic aroma component that is present in coffee (Non-Patent Document 1). Its structure was determined by G. Buchi et al. By them, that is to say, the compound was found to have the structure represented by the following formula, and was named kahweofuran (Non-Patent Document 2).

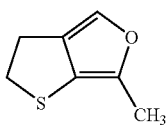

As processes for synthesizing kahweofuran, the process of G. Buchi et al. (Non-Patent Document 2), the process of E. Brenna et al. (Non-Patent Documents 3 and 4), and the process of D. Rewicki et al. (Non-Patent Document 5), are known, but none of them can be said to be efficient. Specifically, the process of G. Buchi et al., which synthesizes kahweofuran in three steps using 4,5-dihydrothiophene-3(2H)-one as a raw material, has problems in that the yield of the Claisen reaction in the first step is low and that two kinds of products are produced in the Grignard reaction in the second step. The process of E. Brenna et al. involves as many as ten steps to produce the compound from the starting material. The process of D. Rewicki et al., although providing a total yield of 12%, has a problem in that it is difficult to obtain 3,4-dibromofuran, which is used as the starting material in the process. Thus, the known synthesis processes cannot be said to be efficient, and have problems when applied to industrial mass-production.

Non-Patent Document 1: Helv. Chim. Acta, 50, 628, (1967)

Non-Patent Document 2: J. Org. Chem., 36, 199, (1971)

Non-Patent Document 3: J. Chem. Research (S), 74, (1998)

Non-Patent Document 4: J. Chem. Research (M), 551, (1998)

Non-Patent Document 5: Liebigs Ann. Chem., 625, (1986)

DISCLOSURE OF THE INVENTION

Problems to be Solved by the Invention

The present invention is made in order to solve the problems of the prior art relating to synthesis of kahweofuran. Specifically, an object of the present invention is to provide an efficient process for synthesizing kahweofuran or an analogue thereof (each referred to as a "kahweofuran compound"). Another object of the present invention is to provide a novel thiophene compound which can be effectively used as a raw material or synthetic intermediate for efficiently synthesizing the kahweofuran compound. Still another object of the present invention is to provide a novel aromatic thiophene compound which is useful as an aroma component and which is produced using the above-mentioned thiophene compound as a raw material or synthetic intermediate, and a production process therefor.

Means for Solving the Problems

In view of the problems as described above, the present inventors conducted extensive research to develop a short and efficient process for producing a kahweofuran compound, which is useful as an aroma component, and found that, when a certain thiophene compound is reacted in a hydrogen atmosphere using a transition metal catalyst, cyclization occurs simultaneously with reduction, making it possible to produce a kahweofuran compound having a 2,3-dihydrothieno[2,3c]furan skeleton in a single step. Further, the present inventors confirmed that the above thiophene compound is a novel compound that can be produced from easily available raw materials by a short process; and that a kahweofuran compound, which is a desired compound of the present invention, can be efficiently produced by the above novel reaction using the thiophene compound as a raw material or synthetic intermediate. The present invention has been accomplished based on these findings.

The present invention provides a novel thiophene compound as defined in the following item 1.

Item 1. A thiophene compound represented by Formula (1):

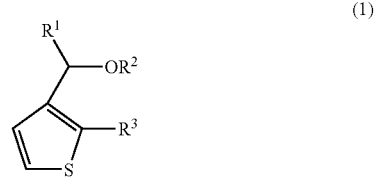

wherein $R^1$ is a hydrogen atom or a $C_1$-$C_4$ lower alkyl group; $R^2$ is a hydrogen atom or an alcohol-protecting group; $R^3$ is a hydrogen atom, —$COR^4$ or —$C(OH)R^5$ (wherein $R^4$ and $R^5$ each represent a $C_1$-$C_4$ lower alkyl group); provided that when $R^2$ and $R^3$ are hydrogen atoms, $R^1$ is not any of a hydrogen atom, methyl group, or n-propyl group.

The present invention also provides processes for producing kahweofuran or analogues thereof using the above novel thiophene compound, as defined in the following items 2 to 4.

Item 2. A method for producing kahweofuran or an analogue thereof represented by Formula (3a), the method comprising the step of reducing and cyclizing a thiophene compound represented by Formula (2) in the presence of a transition metal catalyst in a hydrogen atmosphere:

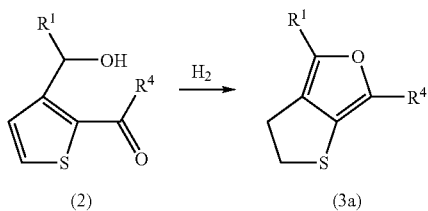

wherein $R^1$ is a hydrogen atom or a $C_1$-$C_4$ lower alkyl group, $R^4$ is a $C_1$-$C_4$ lower alkyl group.

Item 3. The method according to item 2, wherein the transition metal catalyst is a rhodium catalyst.

Item 4. The method for producing kahweofuran or an analogue thereof represented by Formula (3a), the method comprising steps A to D indicated in the scheme given below:

step A: protecting the hydroxy group of compound (4) to obtain compound (5);
step B: acylating compound (5) to obtain compound (6);
step C: deprotecting compound (6) to obtain compound (2); and
step D: reducing and cyclizing compound (2) in the presence of a transition metal catalyst in a hydrogen atmosphere to obtain kahweofuran or analogue thereof (3a);

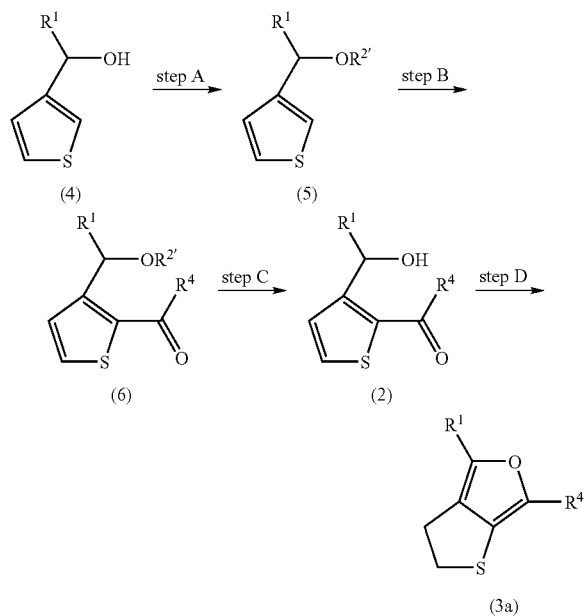

wherein $R^1$ is a hydrogen atom or a $C_1$-$C_4$ lower alkyl group, R2' is an alcohol-protecting group, and $R^4$ is a $C_1$-$C_4$ lower alkyl group.

The present invention also provides a novel kahweofuran analogue as defined in item 5:

Item 5. 4-Methyl-6-ethyl-2,3-dihydrothieno[2,3c]furan, 4-ethyl-6-methyl-2,3-dihydrothieno[2,3c]furan, or 4-ethyl-2,3-dihydrothieno[2,3c]furan.

Further, The present inventors confirmed that a novel aromatic thiophene compound can be produced using the novel thiophene compound defined in item 1 as a raw material. Based on such a finding, the present invention also provides a novel thiophene compound (aromatic thiophene compound) that is useful as an aroma component, and a production method therefor, as defined in items 6 and 7.

Item 6. A thiophene compound represented by Formula (7):

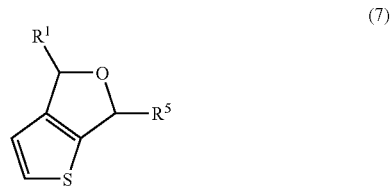

wherein $R^1$ is a hydrogen atom or a $C_1$-$C_4$ lower alkyl group, and $R^5$ is a $C_1$-$C_4$ lower alkyl group).

Item 7. A method for producing thiophene compound (7) according to item 6, the method comprising the step of cyclizing compound (8) shown in the following scheme:

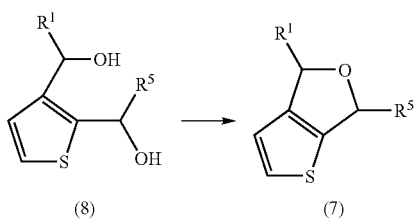

wherein $R^1$ is a hydrogen atom or a $C_1$-$C_4$ lower alkyl group, and $R^5$ is a $C_1$-$C_4$ lower alkyl group.

The above-mentioned kahweofuran and analogue thereof (3a), and the novel thiophene compound (7) defined in item 6, have an aroma and are useful as aroma components. The present invention therefore also provides use of kahweofuran or an analogue thereof and the above novel thiophene compound (7), which are aroma components, as defined in the following items 8 and 9:

Item 8. A flavoring composition comprising $10^{-2}$ to $10^6$ ppb of at least one compound selected from the group consisting of kahweofuran and analogues thereof represented by Formula (3)

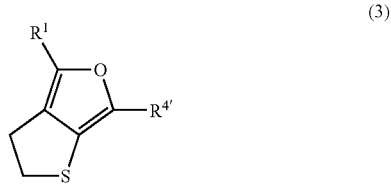

wherein $R^1$ is a hydrogen atom or a $C_1$-$C_4$ lower alkyl group, and R4' is a hydrogen atom or a $C_1$-$C_4$ lower alkyl group, and thiophene compound (7) according to item 6.

Item 9. A food or beverage product comprising $10^{-3}$ to 109 ppb of at least one compound selected from the group consisting of kahweofuran and analogues thereof represented by Formula (3):

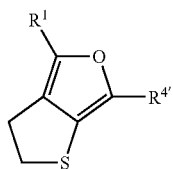

(3)

wherein $R^1$ is a hydrogen atom or a $C_1$-$C_4$ lower alkyl group, and R4' is a hydrogen atom or a $C_1$-$C_4$ lower alkyl group, and thiophene compound (7) according to item 6.

EFFECTS OF THE INVENTION

The present invention provides a novel thiophene compound, and a process for producing kahweofuran or an analogue thereof using the novel thiophene compound as an intermediate material. The novel thiophene compound of the present invention is useful as a synthetic intermediate for a kahweofuran compound, which is an aroma substance. Further, the present invention provides another novel thiophene compound (aromatic thiophene compound) that itself has an aroma and can be effectively used as an aroma component.

BEST MODE FOR CARRYING OUT THE INVENTION (1) Novel Thiophene Compound

The present invention relates to a thiophene compound represented by Formula (1)

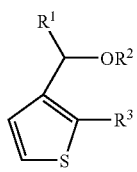

(1)

In Formula (1), $R^1$ is a hydrogen atom or a $C_1$-$C_4$ lower alkyl group. Specific examples of lower alkyl groups include $C_1$-$C_4$ lower alkyl groups, such as methyl, ethyl, n-propyl, isopropyl, n-butyl, isobutyl, sec-butyl, and t-butyl, etc. $R^1$ is preferably a hydrogen atom or a $C_1$ or $C_2$ lower alkyl group, such as methyl, ethyl, or the like.

$R^2$ is a hydrogen atom or an alcohol-protecting group. A wide variety of known alcohol-protecting groups that are used in this field to protect the hydroxy group of alcohols can be used. Specific examples thereof include, but are not limited to, tetrahydrofuranyl (THF) group, tetrahydropyranyl (THP) group, methoxymethyl (MOM) group, t-butyldimethylsilyl (TBDMS) group, acetyl group, ethoxymethyl (EOM) group, benzyloxymethyl (BOM) group, etc., with tetrahydropyranyl (THP) group and methoxymethyl (MOM) group being preferable.

$R^3$ is a hydrogen atom, a group represented by —$COR^4$, or a group represented by —$C(OH)R^5$. $R^4$ and $R^5$ each represent a $C_1$ to $C_4$ lower alkyl group. Specific examples of lower alkyl groups include $C_1$-$C_4$ lower alkyl groups, such as methyl, ethyl, n-propyl, isopropyl, n-butyl, isobutyl, sec-butyl, t-butyl, etc., among which $C_1$ or $C_2$ lower alkyl groups, such as methyl and ethyl, are preferable.

Thiophene compound (1) according to the present invention can be roughly classified into the following three groups (thiophene compounds (A) to (C)).

(i) Thiophene Compound (A)

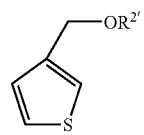

(A)

wherein $R^{2'}$ is an alcohol-protecting group.

Thiophene compound (A) is a compound of Formula (1) in which $R^1$ and $R^3$ each represent a hydrogen atom. The alcohol-protecting group may be any of the above-mentioned examples, with a tetrahydropyranyl (THP) group being preferable. Examples of thiophene compound (A) having such an alcohol-protecting group include 2-(3-thienylmethyloxy)tetrahydro-2H-pyrane (compound (b)) shown in Example 1 (1).

Thiophene compound (A) can be easily synthesized by protecting the hydroxy group of thiophene-3-methanol using a standard method (step A).

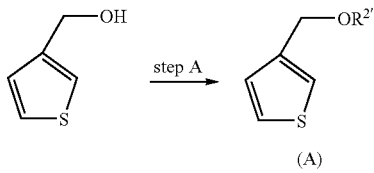

(A)

wherein $R^2$ is an alcohol-protecting group.

Specifically, step A can be carried out by reacting thiophene-3-methanol with an alcohol protecting agent, as shown in Example 1. The reaction conditions are not limited, and the reaction can be performed, for example, under pH conditions that are suitable for the alcohol protecting agent used. Specifically, neutral conditions are suitable when tetrahydrofuran mentioned below is used as an alcohol protecting agent; and acidic conditions are suitable when 3,4-dihydro-2H-pyrane mentioned below is used as an alcohol protecting agent.

The alcohol protecting agent can be selected depending on the alcohol-protecting group to be bonded, and may be, for example, tetrahydrofuran (to bond a THF group), 3,4-dihydro-2H-pyrane (to bond a THP group), chloromethyl methyl ether (to bond a MOM group), t-butyldimethylsilyl chloride (to bond a TBDMS group), acetic anhydride (to bond an acetyl group), chloromethyl ethyl ether (to bond an EOM group), chloromethyl benzyl ether (to bond a BOM group), or the like, with 3,4-dihydro-2H-pyrane or chloromethyl methyl ether being preferable.

The reaction can be carried out usually at $-10°$ C. to $80°$ C., using a solvent, such as dichloromethane, tetrahydrofuran, ethyl acetate, ether, toluene, acetonitrile, pyridine, or the like, which is selected according to the type of alcohol protecting agent used.

When necessary (e.g., when the reaction is carried out under acidic conditions), the reaction can be performed in the presence of an acid catalyst, by adding sulfuric acid, hydrochloric acid, p-toluenesulfonic acid, pyridium p-toluenesulfonate, or like acid catalyst.

(ii) Thiophene Compound (B)

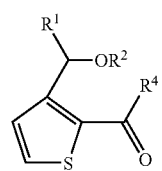
(B)

wherein $R^1$ is a hydrogen atom or a $C_1$-$C_4$ lower alkyl group, $R^2$ is a hydrogen atom or an alcohol-protecting group, and $R^4$ is a $C_1$-$C_4$ lower alkyl group.

Thiophene compound (B) corresponds to a thiophene compound of Formula (1) in which $R^3$ is —$COR^4$. Each of the lower alkyl groups represented by $R^1$ and $R^4$ is preferably a $C_1$ or $C_2$ lower alkyl group, such as methyl or ethyl. The alcohol-protecting group may be any of the alcohol-protecting groups mentioned above, and is preferably a tetrahydropyranyl (THP) group.

Specific examples of thiophene compound (B) include compounds of Formula (B) in which $R^1$ is a hydrogen atom, $R^2$ is an alcohol-protecting group, $R^4$ is a $C_1$ or $C_2$ lower alkyl group, such as methyl or ethyl, i.e., 1-[3-[(tetrahydro-2H-2-pyranyloxy)methyl]-2-thienyl]-1-ethanone (compound (c)) or 1-[3-[(tetrahydro-2H-2-pyranyloxy)methyl]-2-thienyl]-1-propanone (compound (f)); and compounds of Formula (B) in which $R^1$ is a hydrogen atom, $R^2$ is a hydrogen atom, and $R^4$ is a $C_1$ or $C_2$ lower alkyl group, such as methyl or ethyl, i.e., 1-[3-(hydroxymethyl)-2-thienyl]-1-ethanone (compound (d)) or 1-[3-(hydroxymethyl)-2-thienyl]-1-propanone (compound (g)), shown in Examples 1 to 3. Other examples include compounds of Formula (B) in which $R^1$ is a $C_1$ or $C_2$ lower alkyl group, such as methyl or ethyl, and $R^2$ is an alcohol-protecting group, $R^4$ is a $C_1$ or $C_2$ lower alkyl group, such as methyl or ethyl, i.e., 1-[3-[(tetrahydro-2H-2-pyranyloxy)ethyl]-2-thienyl]-1-propanone (compound (D)), 1-[3-[(tetrahydro-2H-2-pyranyloxy)propyl]-2-thienyl]-1-ethanone (compound (U)), and 1-[3-[(tetrahydro-2H-2-pyranyloxy)propyl]-2-thienyl]-1-propanone (compound (X)), shown in Examples 6, 9 and 10. Thiophene compound (B-1) (compound (c), (f)), in which $R^1$ is a hydrogen atom and $R^2$ is an alcohol-protecting group, can be synthesized by acylating the above-mentioned thiophene compound (A) by a standard method (step B), as described in Examples 1 to 3.

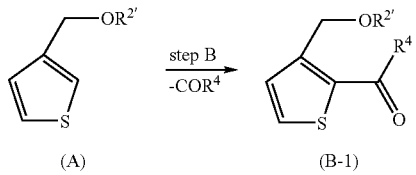

wherein $R^{2'}$ is an alcohol-protecting group and $R^4$ is a $C_1$-$C_4$ lower alkyl group.

The reaction can be performed by reacting thiophene compound (A) with an alkyl metal reagent and then with an acylating reagent, as shown in step B in Examples 1 to 3. The reaction is carried out usually at −100° C. to 20° C., using a solvent, such as tetrahydrofuran, dichloromethane, toluene, or the like, which is selected according to the type of acyl group to be bonded.

The alkyl metal reagent is not limited, and may be, for example, n-butyllithium, sec-butyllithium, or t-butyllithium. Among these, n-butyllithium is preferable. The proportion of alkyl metal reagent is not limited, and may be usually 1 to 1.5 mol, and preferably 1 to 1.1 mol, per mol of thiophene compound (A).

The acylating reagent is also not limited, and examples thereof include acetic anhydride, propionic anhydride, acetyl chloride, and propionyl chloride, with acetic anhydride and propionic anhydride being preferable. The proportion of acylating reagent is not limited, and may be usually 1 to 3 mol, and preferably 1 to 1.2 mol, per mol of thiophene compound (A).

Thiophene compound (B-2) (compounds (d), (g)), in which $R^1$ and $R^2$ each represent a hydrogen atom, can be synthesized by removing the alcohol-protecting group of the above-obtained thiophene compound (B-1) (in which $R^{2'}$ is an alcohol-protecting group) by a standard method, as shown in Examples 1 and 3,

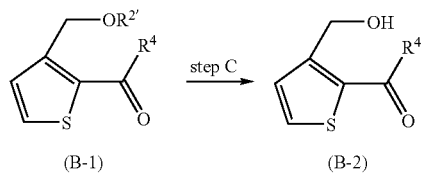

wherein $R^2$ is an alcohol-protecting group and $R^4$ is a $C_1$ to $C_4$ lower alkyl group.

Specifically, as shown in step C in Examples 1 and 3, the alcohol-protecting group can be removed by reacting thiophene compound (B-1) with an organic metal reagent, or by reacting thiophene compound (B-1) with an alcohol in the presence of an acid catalyst. The reaction is carried out usually at −30° C. to 80° C., using a solvent, such as dichloromethane, methanol, ethanol, propanol, toluene, or the like.

The organic metal reagent is not limited, and may be, for example, dimethylaluminum chloride, diethylaluminum chloride, or the like. Among these, dimethylaluminum chloride is preferable. The proportion of organic metal reagent is not limited, and may be usually 1 to 3 mol, and preferably 2 to 2.5 mol, per mol of thiophene compound (B-1).

Examples of acid catalysts include sulfuric acid, hydrochloric acid, p-toluenesulfonic acid, pyridinium p-toluenesulfonate, etc. Examples of alcohols include ethanol, methanol, etc.

Thiophene compound (B) according to the present invention encompasses thiophene compound (B-3), in which $R^1$ and $R^4$ each present $C_1$-$C_4$ lower alkyl groups, such as methyl or the like, and $R^2$ is a hydrogen atom. Specific examples of thiophene compound (B-3) include 1-[3-(1-hydroxyethyl)-2-thienyl]-1-ethanone (compound (j)) shown in Example 4 (2), 1-[3-(1-hydroxyethyl)-2-thienyl]-1-propanone (compound (E)) shown in Example 6 (4), 1-[3-(1-hydroxypropyl)-2-thienyl]-1-ethanone (compound (V)) shown in Example 9 (2), and 1-[3-(1-hydroxypropyl)-2-thienyl]-1-propanone (compound (Y)) shown in Example 10 (2). Such thiophene compound (B-3) (e.g., compound (j) shown in Example 4) can be synthesized by, for example, as shown in Examples 1 to 3, subjecting thiophene-3-methanol to step A (protection of the hydroxy group), step B (acylation), and step C (deprotection) to obtain 2-acylthiophene-3-methanol[1-[2-(hydroxymethyl)-2-thienyl]-1-alkanone] (e.g., compound (c) or (g)), and then oxidizing the obtained 2-acylthiophene-3-methanol (step (i)), followed by alkylation of the obtained aldehyde compound (2-acyl-3-thiophenecarboaldehyde: compound (i)) (step (ii)), as shown in the following reaction scheme.

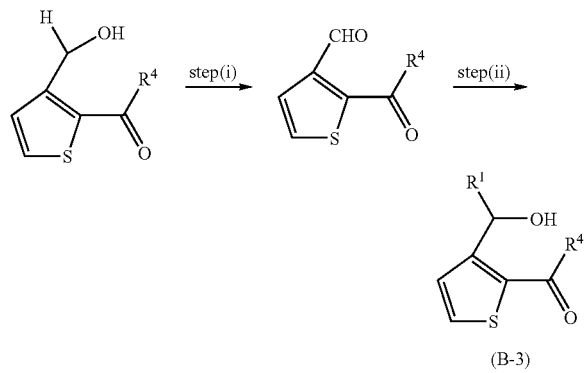

(B-3)

wherein $R^1$ and $R^4$ are the same or different, and each represent a $C_1$-$C_4$ lower alkyl group.

Specifically, step (i) can be carried out by, for example, as described in Example 4 (1), oxidizing 2-acylthiophene-3-methanol (e.g., compound (d)) in the presence of a metal oxide, such as manganese dioxide, magnesium oxide, or the like. The oxidation reaction can also be carried out by a reaction with oxalyl chloride, dicyclohexylcarbodiimide, acid anhydride, chlorine, or the like in dimethylsulfoxide, or by a reaction with dimethylsulfide and N-chlorosuccimide. The reaction is performed usually at −30° C. to 100° C., using a solvent, such as dichloromethane, tetrahydrofuran, ethyl acetate, ether, or dimethyl sulfoxide.

Step (ii) can be carried out by reacting the aldehyde compound obtained in step (i) with an organic metal reagent, as shown in Example 4 (2). The reaction is performed usually at −30° C. to 100° C., using a solvent such as tetrahydrofuran, dichloromethane, ether, toluene, or the like. Examples of usable organic metal reagents include methylmagnesium bromide, ethylmagnesium bromide, propylmagnesium bromide, butylmagnesium bromide, methylmagnesium chloride, ethylmagnesium chloride, etc.

Further, thiophene compound (B-4), in which $R^1$ and $R^4$ each present $C_1$-$C_4$ lower alkyl groups, such as methyl or the like, and $R^2$ is an alcohol-protecting group, can be synthesized by protecting the hydroxy group of thiophene compound (B-3) with an alcohol protecting agent by a standard method.

(B-4)

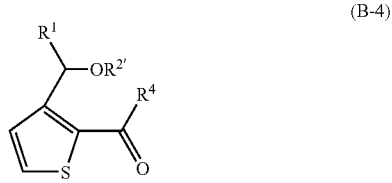

wherein $R^1$ and $R^4$ are the same or different and each represent a $C_1$-$C_4$ lower alkyl group, and $R^2$ is an alcohol-protecting group.

(iii) Thiophene Compound (C)

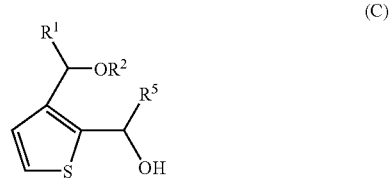

(C)

wherein $R^1$ is a hydrogen atom or a $C_1$-$C_4$ lower alkyl group, $R^2$ is a hydrogen atom or an alcohol-protecting group, and $R^5$ is a $C_1$-$C_4$ lower alkyl group.

Thiophene compound (C) is a thiophene compound represented by Formula (1) in which $R^3$ is —C(OH)$R^5$. The lower alkyl groups represented by $R^1$ and $R^5$ are both preferably $C_1$ or $C_2$ lower alkyl groups, such as methyl or ethyl. The alcohol-protecting group may be any of the alcohol-protecting groups mentioned above, and is preferably a tetrahydropyranyl (THP) group.

Specific suitable examples of thiophene compound (C) include compounds of Formula (C) in which $R^1$ and $R^2$ are both hydrogen atoms, and $R^5$ is a $C_1$ or $C_2$ lower alkyl group, such as methyl or ethyl, i.e., 1-(3-hydroxymethyl-2-thienyl)-1-ethanol (compound (l)) or 1-[(3-hydroxymethyl)-2-thienyl]-1-propanol (compound (n)), as shown in Example 5. Thiophene compound (C-1), in which $R^1$ is a hydrogen atom, $R^2$ is a hydrogen atom or an alcohol-protecting group, and $R^5$ is a lower alkyl group, can be synthesized by reducing thiophene compound (B-1) or (B-2) mentioned above by a standard method (step (iii)), as described in Example 5.

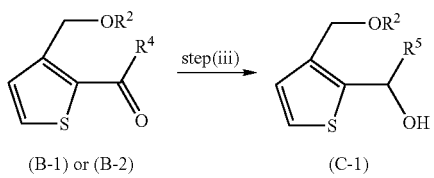

(B-1) or (B-2)    (C-1)

wherein $R^2$ is a hydrogen atom or an alcohol-protecting group, and $R^4$ and $R^5$ are the same and each represent a $C_1$-$C_4$ lower alkyl group.

Thiophene compound (C-2), in which $R^1$ is a lower alkyl group, $R^2$ is a hydrogen atom or an alcohol-protecting group, and $R^5$ is a lower alkyl group, can be synthesized by reducing thiophene compound (B-3) mentioned above by a standard method as described in Example 5 (step (iii)).

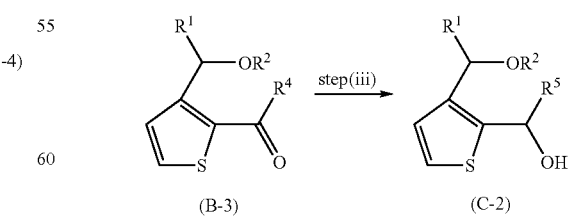

(B-3)    (C-2)

wherein $R^1$ is a $C_1$-$C_4$ lower alkyl group, $R^2$ is a hydrogen atom or an alcohol-protecting group, and $R^4$ and $R^5$ are the same and each represent a $C_1$-$C_4$ lower alkyl group.

The reduction reaction is not limited, and the reduction can be carried out by reacting thiophene compound (B) (thiophene compound (B-1), (B-2), or (B-3)) with, for example, a metal hydride, such as lithium aluminium hydride, sodium borohydride, or the like. The reaction is carried out usually at −20° C. to 50° C., using a solvent, such as methanol, ethanol, tetrahydrofuran, ethyl acetate, ether, toluene, or the like.

In the above methods for producing thiophene compounds, the post-treatment after each reaction is not limited. For example, after completion of the reaction, the reaction mixture can be concentrated under reduced pressure, and subjected to arbitrary purification operations, such as chromatography on silica gel (e.g., preparative silica gel thin-layer chromatography, silica gel column chromatography, etc.), distillation, recrystallization, etc.

Thiophene compound (1) thus obtained can be effectively used as a raw material or synthetic intermediate for efficiently producing kahweofuran or an analogue thereof, each of which is useful as an aroma component, as described hereinafter.

(2) Process for Producing Kahweofuran or Analogue Thereof (2-1) The present invention provides a novel method for producing kahweofuran or an analogue thereof represented by Formula (3a) (hereinafter each sometimes referred to as a kahweofuran compound).

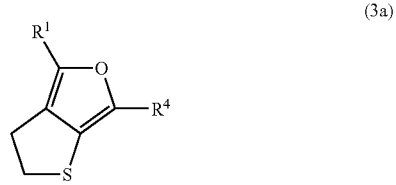

(3a)

wherein $R^1$ is a hydrogen atom or a $C_1$-$C_4$ lower alkyl group, and $R^4$ is a $C_1$-$C_4$ lower alkyl group.

The lower alkyl groups represented by $R^1$ and $R^4$ are the same or different, and each represent a $C_1$-$C_4$ alkyl group, such as methyl, ethyl, n-propyl, isopropyl, n-butyl, isobutyl, sec-butyl, t-butyl, or the like. $C_1$ or $C_2$ lower alkyl groups, such as methyl and ethyl, are preferable. Kahweofuran (chemical name: 6-methyl-2,3-dihydrothieno[2,3c]furan) is a compound with a 2,3-dihydrothieno[2,3c]furan skeleton, which is represented by Formula (3) wherein $R^1$ is a hydrogen atom and $R^4$ is a methyl group (2,3-dihydrothieno[2,3c]furan compound). Preferable examples of analogues of kahweofuran include ethyl kahweofuran (chemical name: 6-ethyl-2,3-dihydrothieno[2,3c]furan) (compound (h)), which is represented by Formula (3) wherein $R^1$ is a hydrogen atom and $R^4$ is an ethyl group; dimethyl kahweofuran (chemical name: 4,6-dimethyl-2,3-dihydrothieno[2,3c]furan) (compound (k)), wherein $R^1$ and $R^4$ are both methyl groups; 4-methyl-6-ethyl-2,3-dihydrothieno[2,3c]furan (compound (F)), wherein $R^1$ is a methyl group and $R^4$ is an ethyl group; 4-ethyl-6-methyl-2,3-dihydrothieno[2,3c]furan (compound (W)), wherein $R^1$ is an ethyl group and $R^4$ is a methyl group; 4,6-diethyl-2,3-dihydrothieno[2,3c]furan (compound (Z)), wherein $R^1$ and $R^2$ are both ethyl groups.

Kahweofuran compound (3) can be synthesized by reducing and cyclizing a thiophene compound represented by Formula (2) (step D). Thiophene compound (2) corresponds to thiophene compound (B-2) or (B-3) mentioned above.

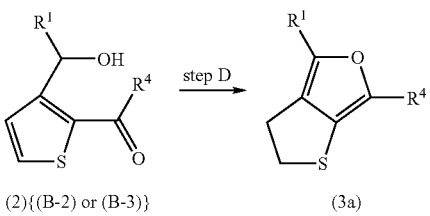

(2){(B-2) or (B-3)}     (3a)

wherein $R^1$ is a hydrogen atom or a $C_1$-$C_4$ lower alkyl group, and $R^4$ is a $C_1$-$C_4$ lower alkyl group.

Specifically, kahweofuran compound (3a) can be synthesized by reacting thiophene compound (2) [(B-2) or (B-3)] mentioned above in a hydrogen atmosphere using a transition metal catalyst.

Usable transition metal catalysts include, but are not limited to, rhodium catalysts, palladium catalysts, etc., among which rhodium catalysts are preferable, and tris(triphenylphosphine) rhodium (I) chloride is particularly preferable. The amount of transition metal catalyst is not limited, and may be usually 0.001 mol to 0.5 mol, and preferably 0.01 to 0.1 mol per mol of thiophene compound (2).

The hydrogen atmosphere is not limited, and is preferably, for example, a hydrogen atmosphere with a gas pressure of 0.1 Mpa to 5 Mpa, and more preferably a hydrogen atmosphere with a gas pressure of 0.5 Mpa to 2 Mpa.

Although there is no limitation on the reaction conditions, the reaction is usually carried out by adding a transition metal catalyst as mentioned above and a solvent to a reactor, and adding a solution of thiophene compound (2) in a solvent, followed by stirring with heating at about 50° C. to about 150° C., and preferably 80° C. to 120° C., for 0.5 to 48 hours, and preferably about 2 to about 24 hours.

The solvent for use in the reaction is not limited, and preferable examples thereof include benzene series solvents such as benzene, toluene, xylene, etc., and chlorine series solvents such as methylene chloride and the like.

After completion of the above reaction, if necessary, the obtained reaction mixture may be concentrated under reduced pressure, and then subjected to arbitrary purification operations such as chromatography on silica gel (e.g., preparative silica gel thin-layer chromatography, silica gel column chromatography, etc.), distillation, recrystallization, etc. Kahweofuran compound (3a), which is a desired compound of the present invention, can be thus obtained. The transition metal catalyst used in the process of the present invention can be recovered by a known method and reused.

Thiophene compound (2) used as a raw material for producing the above kahweofuran compound can be prepared according to the method for producing thiophene compound (B-2) or (B-3) described above.

The production method for kahweofuran compound (3a) of the present invention encompasses the process represented by the following formula:

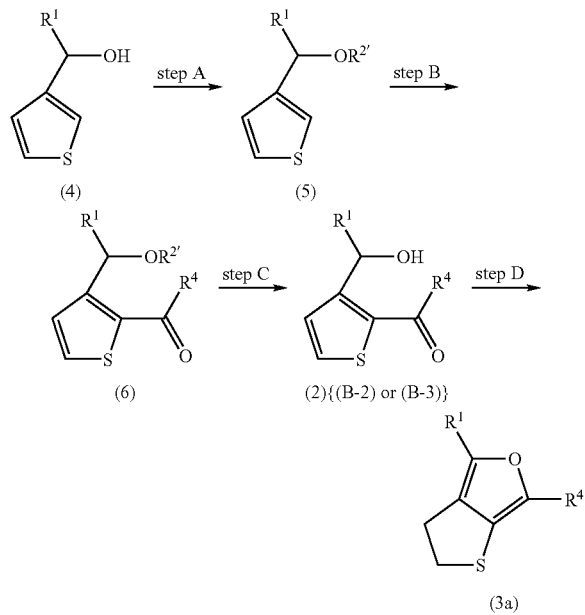

wherein $R^1$ is a hydrogen atom or a $C_1$-$C_4$ lower alkyl group; $R^2$ is an alcohol-protecting group; and $R^4$ is a $C_1$-$C_4$ lower alkyl group.

The above production method can be carried out by the following steps A to D.

Step A: Step A is protection of the hydroxy group of the compound of Formula (4) [thiophene-3-methanol (when $R^1$ is a hydrogen atom) or 3-(1-hydroxyalkyl)thiophene (when $R^1$ is a lower alkyl group)]. Specifically, the step can be performed by reacting compound (4) [thiophene-3-methanol or 3-(1-hydroxyalkyl)thiophene] with an alcohol protecting agent in the presence of an acid catalyst or under neutral or basic conditions. The alcohol protecting agent can be selected depending on the alcohol-protecting group to be bonded. Usable alcohol protecting agents include tetrahydrofuran, 3,4-dihydro-2H-pyrane, chloromethyl methyl ether, t-butyldimethylsilyl chloride, acetic anhydride, chloromethyl ethyl ether, and chloromethyl benzyl ether, among which 3,4-dihydro-2H-pyrane is preferable.

The reaction can be carried out usually at −10° C. to 80° C., using a solvent, such as dichloromethane, tetrahydrofuran, ethyl acetate, ether, toluene, acetonitrile, pyridine, or the like, which is selected according to the alcohol protecting agent used. If necessary, the reaction can be carried out in the presence of an acid catalyst, by adding sulfuric acid, hydrochloric acid, p-toluenesulfonic acid, pyridium p-toluenesulfonate, or like acid catalyst. A compound represented by Formula (5) can thus be obtained.

Step B: Step B is acylation of compound (5) obtained in step A [e.g., when using 3,4-dihydro-2H-pyrane as the alcohol protecting agent, 2-(3-thienylmethyloxy)tetrahydro-2H-pyrane (when $R^1$ is hydrogen) or 2-(1-alkyl-1-(3-thienyl)methyloxy)tetrahydro-2H-pyrane] (when $R^1$ is a lower alkyl group)].

Specifically, the step can be carried out by reacting compound (5) with an alkyl metal reagent, and then with an acylating reagent. The reaction can be performed usually at −100° C. to 20° C. using a solvent, such as tetrahydrofuran, dichloromethane, toluene, or the like.

The alkyl metal reagent is not limited, and may be, for example, n-butyllithium, sec-butyllithium, or t-butyllithium, and is preferably n-butyllithium. The proportion of alkyl metal reagent is not limited, and may be, for example, 1 to 1.5 mol, and preferably 1 to 1.1 mol, per mol of compound (5).

The acylating reagent is not limited, and examples thereof include acetic anhydride, propionic anhydride, acetyl chloride, or propionyl chloride, and is preferably acetic anhydride or propionic anhydride. The proportion of acylating reagent is not limited, and may be, for example, 1 to 3 mol, and preferably 1 to 1.2 mol, per mol of compound (5). A compound represented by Formula (6) can thus be obtained.

Step C: Step C is removal of the alcohol-protecting group (deprotection) of compound (6) obtained in step B.

Specifically, the step can be carried out by reacting compound (6) with an organic metal reagent, or by reacting compound (6) with an alcohol in the presence of an acid catalyst. The reaction is performed usually at −30° C. to 80° C., using a solvent such as dichloromethane, methanol, ethanol, propanol, toluene, or the like.

The organic metal reagent is not limited, and examples thereof include dimethylaluminum chloride, diethylaluminum chloride, etc., among which dimethylaluminum chloride is preferable. The proportion of organic metal reagent is not limited, and may be 1 mol to 3 mol, and preferably 2 to 2.5 mol, per mol of compound (6). Examples of acid catalysts include sulfuric acid, hydrochloric acid, camphorsulfonic acid, pyridinium p-toluenesulfonate, etc. Examples of alcohols include ethanol, methanol, etc. A compound represented by Formula (2) can thus be obtained.

Step D: Step D is reduction and cyclization of compound (2) obtained in step C. The step can be carried out by reacting compound (2) in a hydrogen atmosphere using a transition metal catalyst. The specific procedure, type and proportion of transition metal catalyst, etc., are as described above.

Thus, a kahweofuran compound can be efficiently synthesized using compound (4) [thiophene-3-methanol (when $R^1$ is a hydrogen atom) or 3-(1-hydroxyalkyl)thiophene (when $R^1$ is a lower alkyl group)] as a starting material. Such a process is capable of producing a kahweofuran compound in a short process on a large industrial scale.

Kahweofuran compound (3a) (2,3-dihydrothieno[2,3c]furan compound) thus obtained has an aroma that is characteristic of each type of compound, and is useful as an aroma component. For example, kahweofuran has a roasted nut-like aroma, vegetable-like green aroma, or caramel-like sweet aroma, when it is diluted to 0.000005 wt. % in water; ethyl kahweofuran has a sweet roasty aroma, when it is diluted to 0.000005 wt. % in water; and dimethyl kahweofuran has a raw bean-like aroma with grassy tones, vegetable-like green aroma, or an aroma with freshness, when it is diluted to 0.000005 wt. % in water.

Of kahweofuran compounds (3a), 4-methyl-6-ethyl-2,3-dihydrothieno[2,3c]furan (compound (F)) (Example 6), in which $R^1$ is a methyl group and $R^4$ is an ethyl group; and 4-ethyl-6-methyl-2,3-dihydrothieno[2,3c]furan (compound (W)) (Example 9), in which $R^1$ is an ethyl group and $R^4$ is a methyl group, are novel compounds. Compound (F) has a nut-like aroma, and compound (W) has a spicy aroma. Further, 4,6-diethyl-2,3-dihydrothieno[2,3c]furan (compound (Z)) (Example 10), in which $R^1$ and $R^4$ are both ethyl groups, has a dry nut-like aroma.

(2-2) The present invention provides a production method for a kahweofuran analogue represented by Formula (3b) (hereinafter sometimes referred to as kahweofuran compound (3b)).

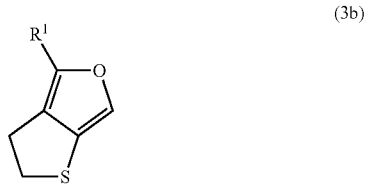

wherein $R^1$ is a $C_1$-$C_4$ lower alkyl group.

Preferable examples of kahweofuran analogue (3b) include 4-methyl-2,3-dihydrothieno[2,3c]furan (compound (L)), which is represented by Formula (3b) wherein $R^1$ is a methyl group; and 4-ethyl-2,3-dihydrothieno[2,3c]furan (compound (T)), wherein $R^1$ is an ethyl group. Among these, 4-ethyl-2,3-dihydrothieno[2,3c]furan is a novel compound.

Kahweofuran compound (3b) can be synthesized by reducing and cyclizing a compound represented by the following Formula (9) (step J).

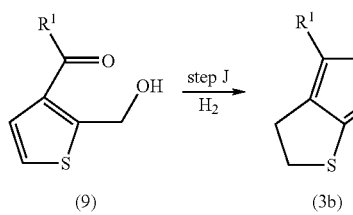

wherein $R^1$ is a $C_1$-$C_4$ lower alkyl group.

Specifically, kahweofuran compound (3b) can be synthesized by reacting compound (9) in a hydrogen atmosphere, using a transition metal catalyst. Usable transition metal catalysts include, but are not limited to, rhodium catalysts, palladium catalysts, etc., among which rhodium catalysts are preferable, and tris(triphenylphosphine)rhodium (I) chloride is particularly preferable. The amount of transition metal catalyst is not limited, and may be usually 0.001 to 0.5 mol, and preferably 0.01 to 0.1 mol, per mol of compound (9).

The hydrogen atmosphere is not limited, and may preferably be, for example, a hydrogen atmosphere with a gas pressure of 0.1 Mpa to 5 Mpa, and more preferably a hydrogen atmosphere with a gas pressure of 0.5 Mpa to 2 Mpa.

Although there is no limitation on the reaction conditions, the reaction is usually carried out by adding a transition metal catalyst as mentioned above and a solvent to a reactor, and adding a solution of compound (9) in a solvent, followed by stirring with heating at about 50° C. to about 150° C., and preferably 80° C. to 120° C., for 0.5 to 48 hours, and preferably about 2 to about 24 hours. The solvent used in the reaction is not limited, and preferable examples thereof include benzene series solvents such as benzene, toluene, xylene, etc., and chlorine series solvents such as methylene chloride and the like.

After completion of the reaction, if necessary, the resulting reaction mixture can be concentrated under reduced pressure, and then subjected to arbitrary purification operations, such as chromatography on silica gel (e.g., preparative silica gel thin-layer chromatography, silica gel column chromatography etc.), distillation, recrystallization, and/or the like, to thereby obtain kahweofuran compound (3b), which is a desired compound of the present invention. The transition metal catalyst used in the present invention can be recovered by a known method, and reused.

The production method for kahweofuran compound (3b) encompasses the process represented by the following scheme.

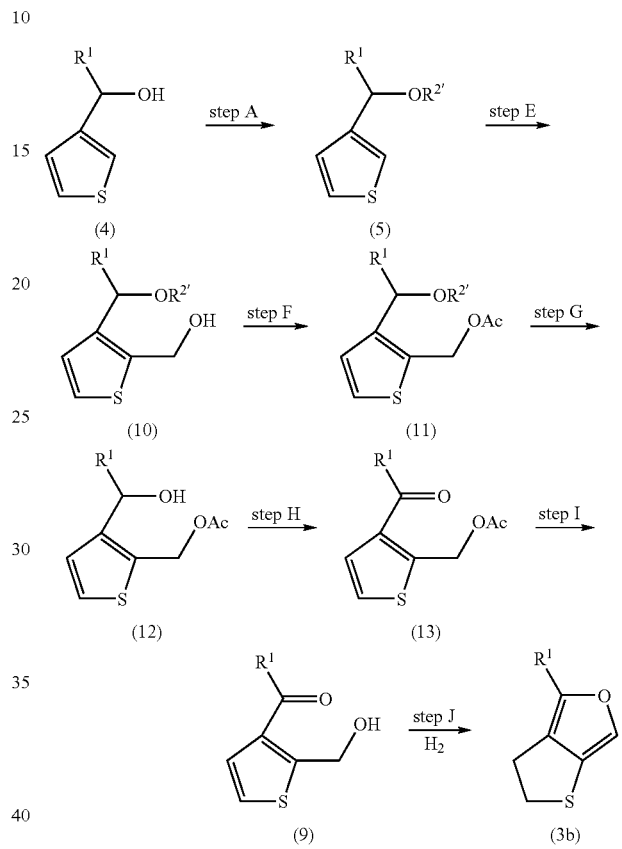

wherein $R^1$ is a $C_1$-$C_4$ lower alkyl group and $R^2$ is an alcohol-protecting group.

The method can be performed by carrying out step A mentioned above, and then steps E to J.

Step E: Step E is hydroxymethylation of compound (5) obtained in step A [e.g., 2-(1-alkyl-1-(3-thienyl)methyloxy) tetrahydro-2H-pyrane when using 3,4-dihydro-2H-pyrane as an alcohol protecting agent].

Specifically, the step can be carried out by reacting compound (5) with an alkyl metal reagent, and then with an aldehyde. The reaction can be performed usually at −100° C. to 50° C. using a solvent, such as tetrahydrofuran, dichloromethane, toluene, or the like.

The alkyl metal reagent is not limited, and examples thereof include n-butyllithium, sec-butyllithium, and t-butyllithium, with n-butyllithium being preferable. The proportion of alkyl metal reagent is not limited, and may usually be 1 mol to 1.5 mol, and preferably 1 mol to 1.1 mol, per mol of compound (5).

Examples of usable aldehydes include, but are not limited to, paraformaldehyde, formaldehyde dimethyl acetal, etc., with paraformaldehyde being preferable. The proportion of aldehyde is not limited, and may be, for example, 1 mol to 3 mol, and preferably 1 mol to 1.2 mol, per mol of compound (5). A compound represented by Formula (10) can thus be obtained.

Step F: Step F is acetylation of compound (10) obtained in step E.

Specifically, the step can be carried out by reacting compound (10) with an alkyl metal reagent, and then with an acetylation reagent. The reaction can be performed usually at −100° C. to 20° C. using a solvent, such as tetrahydrofuran, dichloromethane, toluene, or the like. The alkyl metal reagent may be any of those mentioned above. The acetylation reagent may be, for example, acetic anhydride. The proportion of acetylation reagent is not limited, and may usually be 1 mol to 3 mol, and preferably 1 mol to 1.2 mol, per mol of compound (10). A compound represented by Formula (11) can thus be obtained.

Step G: Step G is removal of an alcohol-protecting group (deprotection) of compound (11) obtained in step F.

Specifically, the step can be carried out by reacting compound (11) with an organic metal reagent, or by reacting compound (11) with an alcohol in the presence of an acid catalyst. The reaction can be carried out usually at −30° C. to 80° C. using a solvent, such as dichloromethane, methanol, ethanol, propanol, toluene, or the like. The organic metal reagent is not limited, and may be, for example, dimethylaluminum chloride, diethylaluminum chloride, or the like, among which dimethylaluminum chloride is preferable. The proportion of organic metal reagent is not limited, and may be usually 1 mol to 3 mol, and preferably 2 mol to 2.5 mol, per mol of compound (11). Examples of acid catalysts include sulfuric acid, hydrochloric acid, p-toluenesulfonic acid, pyridinium p-toluenesulfonate, etc. Examples of alcohols include ethanol, methanol, etc. A compound represented by Formula (12) can thus be obtained.

Step H: Step H is oxidization of the hydroxy group of compound (12) obtained in step G. The step can be carried out by reacting compound (12) with an oxidizing reagent. The conditions for the reaction are not limited. For example, the reaction can be performed usually at −30° C. to 50° C. using a set of dimethyl sulfoxide and oxalyl chloride, magnesium oxide, chromium oxide, pyridinium chlorochromate, pyridinium dichromate, etc. A compound represented by Formula (13) can thus be obtained.

Step I: Step I is deprotection of the acetyl group of compound (13) obtained in step H. Specifically, the step can be carried out by hydrolyzing compound (13) under acidic or basic conditions, or by reacting compound (13) with an alcohol in the presence of a basic catalyst. The reaction can be performed usually at −30° C. to 80° C. using a solvent, such as dichloromethane, methanol, ethanol, propanol, toluene, or the like. A compound represented by Formula (9) can thus be obtained.

Step J: Step J is reduction and cyclization of compound (9) obtained in step I. The step can be carried out by reacting compound (9) in a hydrogen atmosphere, using a transition metal catalyst. The specific procedure, the type and proportion of transition metal catalyst, etc., are as described above.

In the above manner, kahweofuran compound (3b) can be synthesized efficiently, using 3-(1-hydroxyalkyl)-thiophene as a starting material. That is, the process is capable of producing kahweofuran compound (3b) in a short process on a large industrial scale.

Kahweofuran compound (3b) (2,3-dihydrothieno[2,3c]furan compound) thus obtained, like kahweofuran compound (3), has an aroma that is characteristic of each type of compound, and is useful as an aroma component. For example, among kahweofuran compounds (3b), 4-methyl-2,3-dihydrothieno[2,3c]furan (compound (L)) (Example 7), in which $R^1$ is a methyl group, has a roasted sesame-like aroma; and 4-ethyl-2,3-dihydrothieno[2,3c]furan (compound (T)) (Example 8), in which $R^1$ is an ethyl group, has a cooked potato-like aroma.

Thus, since these kahweofuran compounds [kahweofuran compounds (3a) and (3b)] (hereinafter collectively referred to as "kahweofuran compound (3)") are useful as components of flavorings, the present invention also provides a flavoring composition comprising kahweofuran compound (3) as a main flavoring component.

Although the proportion of kahweofuran compound (3) used in the flavoring composition varies depending on the type of kahweofuran compound (3) used, purpose of use, etc., the proportion is, for example, $10^{-9}$ to $10^{-1}$ wt. % ($10^{-2}$ to $10^6$ ppb), and preferably $10^{-5}$ to $10^{-2}$ wt. % ($10^2$ to $10^5$ ppb), of the total weight of the flavoring composition.

Specifically, since kahweofuran and ethyl kahweofuran have a roasty aroma, flavoring compositions containing these kahweofuran compounds are useful for giving the flavors of sesame, coffee, cocoa, chocolate, maple syrup, caramel, tea, nuts, vanilla, meats such as beef and the like, buttermilk, cream, cheese, and fruits such as grape, raspberry, black currant, etc. Since dimethyl kahweofuran has a grassy smell or a vegetable-like green aroma, flavoring compositions containing dimethyl kahweofuran are useful for giving the flavors of green soybeans, and fruits with green aromas such as kiwifruit, melon, watermelon, apple, banana, etc.; tomato, cabbage, cucumber, and like vegetables; and tea.

The present invention further relates to a food or beverage product containing such a flavoring composition. The proportion of kahweofuran compound (3) used in the food or beverage product varies depending on the type of kahweofuran compound (3) used and the type of food or beverage product, and may be, for example, $10^{-12}$ to $10^{-4}$ wt. % ($10^{-5}$ to $10^3$ ppb), preferably $10^{-6}$ to $10^{-1}$ wt. % (10 to $10^6$ ppb), of the total weight of the food or beverage product.

Examples of food and beverage products that can contain kahweofuran compound (3) as a flavoring component are not limited, and include ice cream, ice milk, lact ice (ice cream-like dessert having low milk solids content), sherbet, ice desserts containing no milk, and like frozen desserts; milk beverages, lactic acid bacteria beverages, soft drinks (with or without fruit juices), carbonated beverages, fruit juice beverages, vegetable beverages, vegetable-fruit beverages, sports drinks, powdered beverages, and like beverages; liqueurs and like alcoholic beverages; coffee beverages, black tea beverages, and like coffee or tea beverages; consommés, potages, and like soups; custard puddings, milk puddings, fruit juice-containing puddings, and like puddings; jellies, Bavarian creams, yogurts, and like desserts; chewing gums, bubble gums, and like gums (stick gums, sugar-coated tablet gums); coated chocolates, such as colored sugar-coated-chocolate candies and the like; flavored chocolates, such as strawberry chocolates, blueberry chocolates, melon chocolates, and the like; hard candies (including bonbons, butter candies, marble candies, etc.), soft candies (including caramels, nougats, gummy candies, marshmallows, etc.), drops, taffies, and like candies; hard biscuits, cookies, okaki and senbei (kinds of Japanese rice crackers), and like baked confections; two-layered dressings, oil-free dressings, ketchups, sauces, and like seasoning liquids; strawberry jams, blueberry jams, apple jams, preserves, and like jams; hams, sausages, roast porks, and like processed meats; fish hams, fish sausages, fish paste, boiled fish paste, and like seafood paste products; cheese and like dairy products; etc.

(3) Aromatic Thiophene Compound and Production Method Therefor

The present invention further provides a thiophene compound (aromatic thiophene compound) represented by Formula (7)

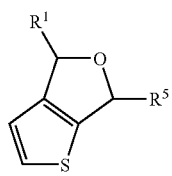

wherein $R^1$ is a hydrogen atom or a $C_1$-$C_4$ lower alkyl group, and $R^5$ is a $C_1$-$C_4$ lower alkyl group.

Since the thiophene compound itself has an aroma, it can be effectively used as a component of a flavoring (flavoring component). The lower alkyl groups represented by $R^1$ and $R^5$ are the same or different, and each may be, for example, a $C_1$-$C_4$ lower alkyl group, such as methyl, ethyl, n-propyl, isopropyl, n-butyl, isobutyl, sec-butyl, t-butyl, or the like. Preferable examples include a $C_1$ or $C_2$ lower alkyl group, such as methyl or ethyl.

A preferable aromatic thiophene compound is 6-methyl-4,6-dihydrothieno[2,3c]furan, in which $R^1$ is hydrogen and $R^5$ is a methyl group.

The aromatic thiophene compound can be produced by reducing compound (2) and then cyclizing the resulting compound (8), as shown in the following scheme:

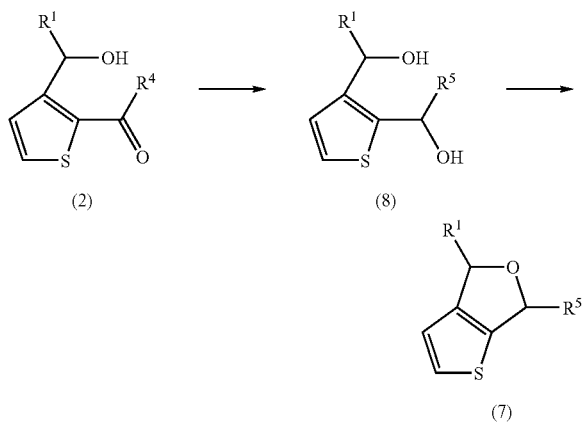

wherein $R^1$ is a hydrogen atom or a $C_1$-$C_4$ lower alkyl group, and $R^4$ and $R^5$ are the same and each represent a $C_1$-$C_4$ lower alkyl group.

The reduction can be carried out by reacting compound (2) with, for example, a metal hydride, such as lithium aluminium hydride, sodium borohydride, or the like, as specifically described in Example 5 (1). The reaction can be performed usually at −20° C. to 50° C. using a solvent, such as methanol, ethanol, tetrahydrofuran, ethyl acetate, ether, toluene, or the like.

The cyclization of compound (8) thus obtained can be performed by, for example, reacting compound (8) with a reagent, such as p-toluenesulfonyl chloride, methanesulfonyl chloride, trifluoromethane sulfonyl chloride, or the like in the presence of an alkyl metal reagent (e.g., n-butyllithium, sec-butyllithium, t-butyllithium, or the like.), as specifically described in Example 5 (2). The reaction can be performed usually at −30° C. to 60° C., using a solvent such as dichloromethane, THF, toluene, or the like.

After completion of the above reaction, if necessary, the obtained reaction mixture may be concentrated under reduced pressure, and subjected to arbitrary purification operations, such as chromatography on silica gel (e.g., preparative silica gel thin-layer chromatography, silica gel column chromatography, etc.), distillation, recrystallization, and/or the like. Aromatic thiophene compound (7), which is a desired compound of the present invention, can be thus obtained.

In such a manner, aromatic thiophene compound (7) can be efficiently synthesized using compound (2) as a raw material, and a synthesis yield of about 30% or higher can be achieved by adjusting the reaction conditions. That is, the method is capable of producing aromatic thiophene compound (7) in a short process on a large industrial scale.

Aromatic thiophene compound (7) thus obtained has an aroma that is characteristic of each type of compound, and is useful as an aroma component. For example, 6-methyl-4,6-dihydrothieno[2,3c]furan, which is one type of aromatic thiophene compound (7), has a fruity sweet aroma, green aroma, or coffee-like aroma, when it is diluted to 0.0035 wt. % in water.

Since aromatic thiophene compound (7) is useful as a component of a flavoring as described above, the present invention also provides a flavoring composition comprising aromatic thiophene compound (7) as a main flavoring component.

Although the proportion of aromatic thiophene compound (7) in the flavoring composition varies depending on the type of aromatic thiophene compound (7) and the purpose of use, the proportion is, for example, $10^{-9}$ to $10^{-1}$ wt. % ($10^{-2}$ to $10^6$ ppb), and preferably $10^{-5}$ to $10^{-2}$ wt. % ($10^2$ to $10^5$ ppb), of the total weight of the flavoring composition.

Specifically, since [6-methyl-4,6-dihydrothieno[2,3c]furan] has a fruity sweet aroma, green aroma, coffee-like aroma, and the like, a flavoring composition containing 6-methyl-4,6-dihydrothieno[2,3c]furan is useful as a coffee or cocoa flavoring, or a melon or watermelon flavoring.

The present invention further relates to a food or beverage product containing such a flavoring composition. Although the proportion of aromatic thiophene compound (7) contained in the food or beverage product varies depending on the type of aromatic thiophene compound (7) and the type of food or beverage product, the proportion is, for example, $10^{-12}$ to $10^{-3}$ wt. % ($10^{-5}$ to $10^4$ ppb), and preferably $10^{-8}$ to $10^{-4}$ wt. % ($10^{-1}$ to $10^3$ ppb), of the total weight of the food or beverage product.

Examples of food and beverage products that can contain aromatic thiophene compound (7) as a flavoring component include those mentioned above as food and beverage products that can contain kahweofuran compound (3).

EXAMPLES

Hereinafter, the present invention will be explained with reference to the following examples, but is not limited thereto.

Example 1

Synthesis of Kahweofuran (Method 1)

Kahweofuran (compound (e)) was produced from thiophene 3-methanol (compound (a)) according to the following formula. THP represents a tetrahydropyranyl group in the formula.

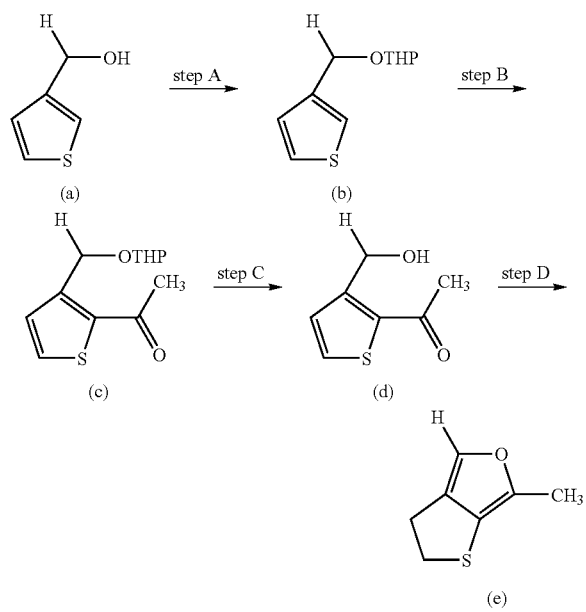

(1) Step A: Protection of the hydroxy group of thiophene-3-methanol

Synthesis of 2-(3-thienylmethyloxy)tetrahydro-2H-pyrane (Compound (b))

To 4.56 g (40 mmol) of thiophene-3-methanol (compound (a)) were added 3.36 g (40 mmol) of 3,4-dihydro-2H-pyrane, 80 ml of dichloromethane solution, and subsequently 0.25 g (1 mmol) of pyridinium p-toluenesulfonate. After stirring the resultant mixed liquid at room temperature for 30 minutes, the solution was distilled off under reduced pressure. The obtained residue was purified by silica gel column chromatography (hexane:ethyl acetate=10:1), to yield, as a colorless oil-like substance, 2-(3-thienylmethyloxy) tetrahydro-2H-pyrane (compound (b), 7.92 g, 100% yield) in which the hydroxy group of thiophene-3-methanol was protected. The physical properties of the obtained 2-(3-thienylmethyloxy) tetrahydro-2H-pyrane are shown below:

$^1$H NMR (CDCl$_3$, 400 MHz, (ppm): 7.30 (dd, J=3.2, 4.8 Hz, 1H), 7.25 (dd, J=3.2, 1.2 Hz, 1H), 7.09 (dd, J=1.2, 4.8 Hz, 1H), 4.77 (d, J=12.4 Hz, 2H), 4.70 (t, J=4 Hz, 1H), 4.54 (d, J=12.4 Hz, 2H), 3.91 (m, 1H), 1.88-1.51 (m, 6H);

$^{13}$C NMR (CDCl$_3$, 100 MHz, (ppm) 139.25, 127.35, 125.74, 122.67, 97.43, 66.99, 62.02, 30.44, 25.42, 19.25;

MS (m/e) 198 (M$^+$);

IR (neat) ($_{max}$ 2945, 2872, 2247, 1466, 1454, 1440, 1120, 1030, 908, 736 cm$^{-1}$.

(2) Step B: Acylation

Synthesis of 1-[3-[(tetrahydro-2H-2-pyranyloxy) methyl]-2-thienyl]-1-ethanone (Compound (c))

0.792 g (4 mmol) of the above-obtained 2-(3-thienylmethyloxy)tetrahydro-2H-pyrane (compound (b)) was dissolved in 80 ml of tetrahydrofuran (THF) solution. To the resultant solution was added dropwise 2.5 ml of n-butyllithium (1.6M hexane solution, 4 mmol) under an argon atmosphere cooled at −78° C. 30 minutes later, 0.408 g (4 mmol) of acetic anhydride was added to the solution, and stirred for 30 minutes. Thereafter, the resulting mixture was returned to room temperature, and further stirred for 30 minutes. Subsequently, the solution was washed with a saturated sodium chloride solution, and the organic layer was dried over anhydrous magnesium sulfate. Thereafter, the solvent was distilled off under reduced pressure. The obtained residue was purified by silica gel column chromatography (hexane:ethyl acetate=10:1), to yield, as a colorless oil-like substance, 1-[3-[(tetrahydro-2H-2-pyranyloxy)methyl]-2-thienyl]-1-ethanone (compound (c), 0.653 g, 68% yield). The physical properties of the obtained 1-[3-[(tetrahydro-2H-2-pyranyloxy) methyl]-2-thienyl]-1-ethanone are shown below:

$^1$H NMR (CDCl$_3$, 400 MHz, (ppm): 7.47 (d, J=5.2 Hz, 1H), 7.34 (d, J=5.2 Hz, 1H), 5.07 (d, J=15.2 Hz, 2H), 4.91 (d, J=15.2 Hz, 2H), 4.74 (t, J=4 Hz, 1H), 3.89 (m, 1H), 3.54 (m, 1H), 2.52 (s, 3H), 1.90-1.52 (m, 6H);

$^{13}$C NMR (CDCl$_3$, 100 MHz), (ppm) 190.68, 147.40, 129.99, 129.53, 98.52, 65.29, 62.21, 30.50, 29.17, 25.23, 22.88, 19.41;

MS (m/e) 240 (M+);

IR (neat) ($_{max}$2943, 2870, 2249, 1660 1525, 1415, 1122, 1068, 910, 731 cm$^{-1}$.

(3) Step C: Deprotection

Synthesis of 1-[3-(hydroxymethyl)-2-thienyl]-1-ethanone (Compound (d))

1.44 g (6 mmol) of the 1-[3-[(tetrahydro-2H-2-pyranyl oxy)methyl]-2-thienyl]-1-ethanone (compound (c)) prepared in step B was dissolved in dichloromethane. To 60 ml of this solution was added dropwise 12 ml (12 mmol) of 1M hexane solution of dimethyl aluminum chloride while stirring at −25° C. After the dropwise adding was completed, the solution was returned to room temperature and further stirred for 1 hour. Subsequently, an aqueous saturated sodium hydrogencarbonate solution was added to the solution to terminate the reaction, followed by filtration through Celite. After washing the separated organic layer with a saturated sodium chloride solution, magnesium sulfate was added for drying, and then the solvent was distilled off under reduced pressure. The obtained residue was purified by silica gel column chromatography (hexane:ethyl acetate=2:1), to yield, as a colorless oil-like substance, 1-[3-(hydroxymethyl)-2-thienyl]-1-ethanone (compound (d), 0.767 g, 82% yield). The physical properties of the obtained 1-[3-(hydroxymethyl)-2-thienyl]-1-ethanone are shown below:

$^1$H NMR (CDCl$_3$, 400 MHz, (ppm): 7.49 (d, J=4.8 Hz, 1H), 7.13 (d, J=4.8 Hz, 1H), 4.74 (d, J=5.6 Hz, 2H), 4.24 (t, J=5.6 Hz, OH, 1H), 2.58 (s, 3H);

$^{13}$C NMR (CDCl$_3$, 100 MHz (ppm) 192.43, 149.98, 136.57, 130.91, 130.51, 59.98, 29.09;

MS (m/e) 156 (M$^+$);

IR (neat) ($_{max}$3441, 2253, 1651, 1518, 1413, 1263, 1032, 908, 733 cm$^{-1}$.

(4) Step D: Cyclization with Reduction

Synthesis of Kahweofuran (Compound (e))

The compound (d) (312 mg (2 mmol)) prepared in step C was dissolved in 10 ml of benzene solution. Subsequently, 92 mg (0.1 mmol) of tris(triphenylphosphine)rhodium (I) chloride was added to the solution. The solution was stirred under heating at 100° C. under a hydrogen atmosphere of 1 Mpa for 24 hours. The solution was condensed to obtain a residue. The residue was purified by silica gel column chromatography (pentane:ether=100:1) to yield, as a colorless oil-like substance, 142 mg of 6-methyl-2,3-dihydrothieno[2,3c]furan (kahweofuran, compound (e), 51% yield). The physical properties of 6-methyl-2,3-dihydrothieno[2,3c]furan are shown below.

$^1$H NMR (CDCl$_3$, 400 MHz, (ppm): 6.98 (t, J=1.6 Hz, 1H), 3.62 (t, J=7.2 Hz, 2H), 2.87 (dt, J=1.6 7.2 Hz, 2H), 2.20 (s, 3H);

$^{13}$C NMR CDCl$_3$, 100 MHz, (ppm) 140.22, 131.61, 128.27, 122.11, 41.99, 26.70, 12.53;

MS (m/e) 140 (M);

IR (neat) ($_{max}$2982, 2916, 1631, 1577, 1433, 1265, 1103, 920, 733 cm$^{-1}$.

Example 2

Synthesis of Kahweofuran (Method 2)

Kahweofuran (compound (e)) was produced from thiophene-3-methanol (compound (a)) according to the following scheme.

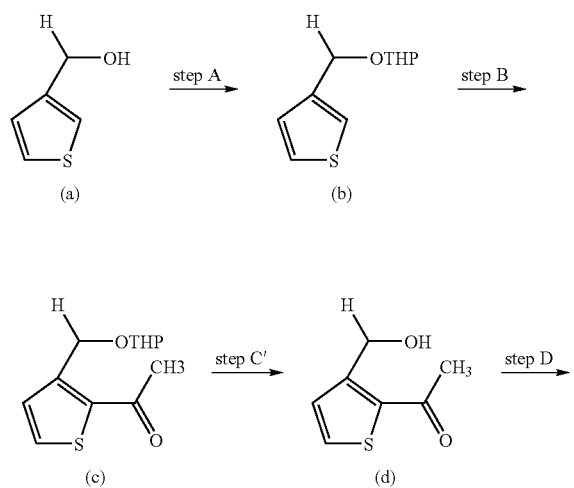

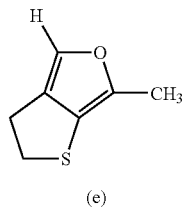

(e)

(1) Step A: Protection of the Hydroxy Group of thiophene-3-methanol

Synthesis of 2-(3-thienylmethyloxy) tetrahydro-2H-pyrane (Compound b)

According to step A described in Example 1,2-(3-thienyl-methyloxy)tetrahydro-2H-pyrane (compound (b)) was synthesized from thiophene-3-methanol (compound (a)).

(2) Step B: Acylation

Synthesis of 1-[3-[(tetrahydro-2H-2-pyranyloxy) methyl]-2-thienyl]-1-ethanone (Compound (c))

According to step B described in Example 1, 1-[3-[(tetrahydro-2H-2-pyranyloxy)methyl]-2-thienyl]-1-ethanone (compound (c)) was produced from 2-(3-thienyl methyloxy) tetrahydro-2H-pyrane (compound (b)).

(3) Step C': Deprotection

Synthesis of 1-[3-(hydroxymethyl)-2-thienyl]-1-ethanone (Compound (d))

The above-prepared 1-[3-[(tetrahydro-2H-2-pyranyloxy) methyl]-2-thienyl]-1-ethanone (compound (c), 2.4 g, 10 mmol) was dissolved in methanol, and camphor sulfonic acid was added thereto at room temperature while stirring. After stirring for 15 minutes, 1.38 g (10 mmol) of potassium carbonate was added to terminate the reaction. After filtering the reaction solution, the filtrate was distilled off under reduced pressure. The obtained residue was purified by silica gel column chromatography (hexane:ethyl acetate=2:1) to yield, as a colorless oil-like substance, 1-[3-(hydroxymethyl)-2-thienyl]-1-ethanone (compound (d), 1.38 g, 88% yield). The physical properties of 1-[3-(hydroxymethyl)-2-thienyl]-1-ethanone are shown below:

$^1$H NMR (CDCl$_3$, 400 MHz, (ppm): 7.49 (d, J=4.8 Hz, 1H), 7.13 (d, J=4.8 Hz, 1H), 4.74 (d, J=5.6 Hz, 2H), 4.24 (t, J=5.6 Hz, OH, 1H), 2.58 (s, 3H);

$^{13}$C NMR (CDCl$_3$, 100 MHz, (ppm) 192.43, 149.98, 136.57, 130.91, 130.51, 59.98, 29.09;

MS (m/e) 156 (M$^+$);

IR (neat) ($_{max}$3441, 2253, 1651, 1518, 1413, 1263, 1032, 908, 733 cm$^{-1}$.

(4) Step D: Reduction with Cyclization

Synthesis of Kahweofuran (Compound (e))

The compound (d) prepared in the above-mentioned step C' was subjected to reduction and cyclization according to the procedure of step D described in Example 1, to yield, as a colorless oil-like substance, 142 mg of 6-methyl-2,3-dihydrothieno[2,3c]furan (kahweofuran, compound (e), 51% yield). The physical properties of the obtained 6-methyl-2,3-dihydrothieno[2,3c]furan (kahweofuran) are shown below:

$^1$H NMR (CDCl$_3$, 400 MHz, (ppm): 6.98 (t, J=1.6 Hz, 1H), 3.62 (t, J=7.2 Hz, 2H), 2.87 (dt, J=1.6 7.2 Hz, 2H), 2.20 (s, 3H);

$^{13}$C NMR (CDCl$_3$, 100 MHz, (ppm) 140.22, 131.61, 128.27, 122.11, 41.99, 26.70, 12.53;

MS (m/e) 140 (M);

IR (neat) ($_{max}$2982, 2916, 1631, 1577, 1433, 1265, 1103, 920, 733 cm$^{-1}$.

Example 3

Synthesis of 6-ethyl-2,3-dihydrothieno[2, 3c]furan 6-ethyl-2,3-dihydrothieno[2,3c]furan (compound (h)) was produced from thiophene-3-methanol (compound (a)) according to the following scheme.

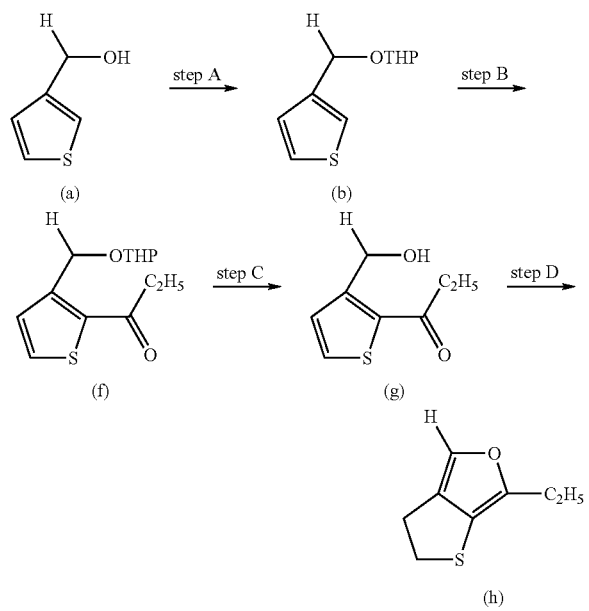

(1) Step A: Protection of the Hydroxy Group of thiophene-3-methanol

Synthesis of 2-(3-thienylmethyloxy) tetrahydro-2H-pyrane (Compound (b))

According to step A of Example 1, 2-(3-thienylmethyloxy) tetrahydro-2H-pyrane (compound (b)) was produced from 4.56 g (40 mmol) of thiophene-3-methanol (compound (a)).

(2) Step B: Acylation

Synthesis of 1-[3-[(tetrahydro-2H-2-pyranyloxy) methyl]-2-thienyl]-1-Propanone (Compound (f))

According to step B of Example 2, using 0.792 g (4 mmol) of the above-prepared 2-(3-thienylmethyloxy)tetrahydro-2H-pyrane (compound (b)), 1-[3-[(tetrahydro-2H-2-pyranyloxy)methyl]-2-thienyl]-1-propanone (compound (f), 0.686 g, 65% yield) was obtained. The physical properties of the obtained 1-[3-[(tetrahydro-2H-2-pyranyloxy)methyl]-2-thienyl]-1-propanone are shown below.

$^1$H NMR (CDCl$_3$, 400 MHz, (ppm): 7.45 (d, J=4.8 Hz, 1H), 7.36 (d, J=4.8 Hz, 1H), 5.10 (d, J=14.8 Hz, 2H), 4.95 (d, J=15.2 Hz, 2H), 4.74 (t, J=4 Hz, 1H), 3.92 (m, 1H), 3.537 (m, 1H), 2.89 (q, J=7.2 Hz, 2H), 1.91-1.53 (m, 6H), 1.21 (t, J=7.2 Hz, 3H);

$^{13}$C NMR (CDCl$_3$, 100 MHz, (ppm) 193.91, 147.41, 129.46, 129.29, 121.71, 98.51, 65.46, 62.22, 34.62, 30.48, 25.37, 19.42, 8.28;

MS (m/e) 254 (M$^+$);

IR (neat) ($_{max}$2943, 2874, 2251, 1662, 1525, 1417, 1203, 1122, 1068, 1035, 910, 733 cm$^{-1}$.

(3) Step (C): Deprotection

Synthesis of 1-[3-(hydroxymethyl)-2-thienyl]-1-propanone (Compound (g))

Into dichloromethane was dissolved 1.44 g (6 mmol) of the 1-[3-[(tetrahydro-2H-2-pyranyloxy)methyl]-2-thienyl]-1-propanone (compound (f)) prepared in step B. To 60 ml of this solution was added dropwise 12 ml (12 mmol) of 1M hexane solution of dimethyl aluminium chloride while stirring at −25° C. After the dropwise adding was completed, the solution was returned to room temperature and further stirred for 1 hour. Subsequently, an aqueous saturated sodium hydrogencarbonate solution was added to the solution to terminate the reaction, followed by filtration through Celite. The separated organic layer was washed with a saturated sodium chloride solution, and magnesium sulfate was added for drying. The solvent was distilled off under reduced pressure. The obtained residue was purified by silica gel column chromatography (hexane:ethyl acetate=2:1), to yield, as a colorless oil-like substance, 1-[3-(hydroxymethyl)-2-thienyl]-1-propanone (compound (g), 0.595 g, 88% yield). The physical properties of the obtained 1-[3-(hydroxymethyl)-2-thienyl]-1-propanone are shown below:

$^1$H NMR (CDCl$_3$, 400 MHz, (ppm) 7.45 (d, J=4.8 Hz, 1H), 7.10 (d, J=4.8 Hz, 1H), 4.72 (d, J=7.6 Hz, 2H), 4.26 (t, J=7.6 Hz, OH, 1H), 2.92 (q, J=7.2 Hz, 2H), 1.21 (t, J=7.2 Hz, 3H);

$^{13}$CNMR (CDCl$_3$, 100 MHz, (ppm) 195.40, 149.80, 137.25, 130.55, 130.39, 60.01, 34.71, 8.43;

MS (m/e) 170 (M$^+$);

IR (neat) ($_{max}$3410, 2254, 1653, 1518, 1413, 1217, 1028, 908, 734$^{cm-1}$.

(4) Step D: Cyclization with Reduction

Synthesis of 6-ethyl-2,3-dihydrothieno[2,3c]furan (Compound (h))

The compound (g) prepared in the above-mentioned step C was subjected to reduction and cyclization according to the procedure of step D described in Example 1, to yield, as a colorless oil-like substance, 6-ethyl-2,3-dihydrothieno[2,3c] furan (compound (h), 54% yield). The physical properties of the obtained 6-ethyl-2,3-dihydrothieno[2,3c]furan are shown below:

$^1$H NMR (CDCl$_3$, 400 MHz, (ppm) 6.980 (t, J=1.6 Hz, 1H), 3.61 (t, J=7.2 Hz, 2H), 2.86 (dt, J=1.6 7.2 Hz, 2H), 2.58 (q, J=7.6 Hz, 2H), 1.22 (t, J=7.6 Hz, 3H);

$^{13}$CNMR (CDCl$_3$, 100 MHz, (ppm) 145.30, 131.44, 126.56, 120.98, 41.76, 25.26, 20.17, 11.40;

MS (m/e) 154 (M$^+$);

IR (neat) ($_{max}$2972, 2935, 2849, 1627, 1573, 1460, 1265, 1109, 949, 754 cm$^{-1}$.

Example 4

Synthesis of 4,6-dimethyl-2,3-dihydrothieno[2,3c]furan 4,6-dimethyl-2,3-dihydrothieno[2,3c]furan (compound (k)) was produced from 1-[3-(hydroxymethyl)-2-thienyl]-1-ethanone[2-acetyl-thiophene-3-methanol (compound (d))] according to the following scheme. 1-[3-(hydroxymethyl)-2-thienyl]-1-ethanone (compound (d)) can be prepared in Example 1 (3) or Example 2 (3).

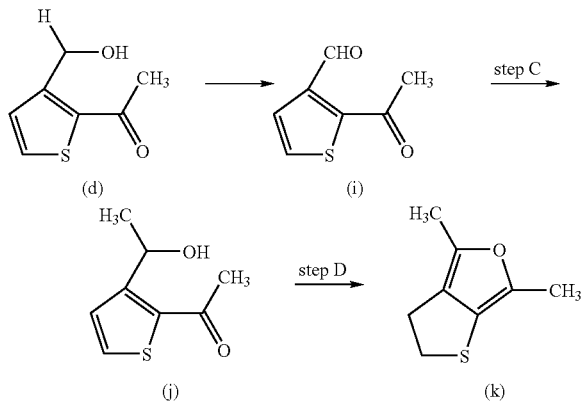

(1) Synthesis of 2-acetyl-3-thiophenecarboxaldehyde (Compound (i))

69.5 g of magnesium oxide (IV) was added to 100 ml of a dichloromethane solution comprising 1.106 g (7 mmol) of 1-[3-(hydroxymethyl)-2-thienyl]-1-ethanone [2-acetyl-thiophene-3-methanol (compound (d))], followed by vigorous stirring at room temperature for 20 minutes. The solution was filtered, and the filtrate was condensed under reduced pressure. The obtained residue was purified by silica gel column chromatography (pentane:ether=2:1), to yield, as a pale yellow oil-like substance, 1.066 g of 2-acetyl-3-thiophenecarboxaldehyde (compound (i), 99% yield). The physical properties of this compound are shown below:

$^1$H NMR (CDCl$_3$, 400 MHz, (ppm); 10.56 (s, 1H) 7.64 (d, J=5.2 Hz, 1H), 7.46 (d, J=5.2 Hz, 1H), 2.65 (s, 3H);

$^{13}$C NMR (CDCl$_3$, 100 MHz, (ppm) 187.20, 184.60, 129.60, 129.54, 128.54, 124.20, 29.69;

MS (m/e) 154 (M$^+$);

IR (neat) ($_{max}$3099, 3086, 1672, 1514, 1423, 1242, 1014, 839, 756 cm$^{-1}$.

(2) Synthesis of 1-[3-(1-hydroxyethyl)-2-thienyl]-1-ethanone (Compound (j))

3 ml (3 mmol) of a 1M THF solution of methyl magnesium bromide was added dropwise to 30 ml of THF solution comprising 0.462 g (3 mmol) of the above-obtained 2-acetyl-3-thiophenecarboxaldehyde (compound (i)) while cooling at −78° C. The solution was returned to room temperature, and further stirred for 30 minutes. After adding 30 ml of ether, the solution was successively washed with an aqueous saturated ammonium chloride solution and a saturated sodium chloride solution, and dried over anhydrous magnesium sulfate. Thereafter, the solvent was distilled off under reduced pressure. The obtained residue was purified by silica gel column chromatography (hexane:ethyl acetate=5:1), to yield, as a colorless oil-like substance, 0.286 g of 1-[3-(1-hydroxyethyl)-2-thienyl]-1-ethanone (compound (j), 56% yield). The physical properties of this compound are shown below:

$^1$H NMR (CDCl$_3$, 400 MHz, (ppm): 7.49 (d, J=5.2 Hz, 1H), 7.18 (d, J=5.2 Hz, 1H), 5.15 (m, J=6.4 Hz, 1H), 4.65 (d, J=6.4 Hz, OH, 1H), 2.59 (s, 3H), 1.52 (d, J=6.4 Hz, 3H);

$^{13}$C NMR (CDCl$_3$, 100 MHz, (ppm) 192.51, 154.51, 136.64, 130.90, 129.06, 65.25, 29.40, 22.38;

MS (m/e) 170 (M$^+$);

IR (neat) ($_{max}$3427, 2982, 2251, 1649, 1514, 1410, 1244, 1113, 910, 734 cm$^{-1}$.

(3) Reduction with Cyclization

Synthesis of 4,6-dimethyl-2,3-dihydrothieno[2,3c]furan (compound (k))

The 1-[3-(1-hydroxyethyl)-2-thienyl]-1-ethanone (compound (j)) prepared in step (2) was subjected to reduction and cyclization according to the procedure of step D described in Example 1, to yield, as a colorless oil-like substance, 4,6-dimethyl-2,3-dihydrothieno[2,3c]furan (compound (k), 58% yield). The physical properties of this compound are shown below:

$^1$H NMR (CDCl$_3$, 400 MHz, (ppm) 3.58 (t, J=7.2 Hz, 2H), 2.76 (t, J=7.2 Hz, 2H), 2.15 (s, 6H);

$^{13}$C NMR CDCl$_3$, 100 MHz (ppm) 140.53, 138.16, 126.64, 117.47, 42.05, 25.51, 12.71, 12.61;

MS (m/e) 154 (M$^+$);

IR (neat) ($_{max}$2918, 2878, 2247, 1660, 1558, 1435, 1217, 1113, 1074, 908, 733 cm$^{-1}$.

Example 5

(A) Synthesis of 6-methyl-4,6-dihydrothieno[2,3c]furan 6-methyl-4,6-dihydrothieno[2,3c]furan was synthesized according to the following scheme.

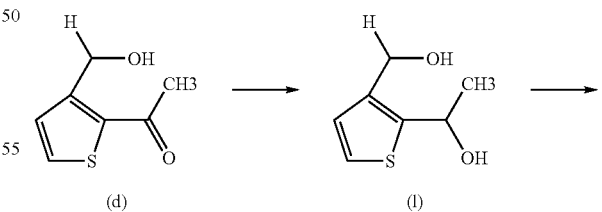

(1) Reduction Reaction

To 20 ml of THF solution containing 0.624 g (4 mmol) of 1-[3-(hydroxymethyl)-2-thienyl]-1-ethanone[2-acetyl-thiophene-3-methanol (compound (d))], 0.152 g (4 mmol) of lithium aluminum hydride was added dropwise while stirring at 0° C. After further stirring the solution for 10 minutes, ethyl acetate was added to the resultant solution to terminate the reaction, followed by filtration through Celite. The organic layer was washed with a saturated sodium chloride solution, and dried over magnesium sulfate, and then the solvent was distilled off under reduced pressure. The obtained residue was purified by column chromatography (hexane:ethyl acetate=1:1), to yield, as a colorless oil-like substance, 0.62 g (a compound (l), 98% yield) of 1-{3-(hydroxymethyl)-2-thienyl]-1-ethanol. The physical properties of this compound are shown below:

$^1$H NMR (CDCl$_3$, 400 MHz, δ ppm) 7.15 (d, J=4.8 Hz, 1H), 6.96 (d, J=4.8 Hz, 1H), 5.20 (q, J=6.4 Hz, 1H), 4.67 (d, J=8.4 Hz, 1H), 4.61 (d, J=8.4 Hz, 1H), 3.34 (w, OH, 1H), 2.88 (w, OH, 1H), 1.61 (d, J=6.4 Hz, 3H);

$^{13}$C NMR (CDCl$_3$, 100 MHz, δ ppm) 145.80, 132.23, 128.83, 122.96, 63.48, 57.68, 24.06;

MS (m/e) 158 (M$^+$);

IR (neat)($_{max}$3339, 2974, 1437, 1068, 995, 910, 734 cm$^{-1}$.

(2) Cyclization

To 20 ml of THF solution containing 0.316 g of 1-{3-(hydroxymethyl)-2-thienyl]-1-ethanol (compound (l), 2 mmol), 1.25 ml (1.6M in hexane, 2 mmol) of n-butyllithium was added dropwise at 0° C. under an argon flow. 5 minutes later, 0.38 g of p-toluenesulfonyl chloride (2 mmol) was added to the solution. Then, the solution was returned to room temperature and stirred for 1 hour. The solution was again cooled to 0° C., and 1.25 ml (1.6M in hexane, 2 mmol) of n-butyllithium was added dropwise. After the dropwise adding was completed, the solution was stirred at room temperature for 18 hours. The solution was washed with a saturated sodium chloride solution, and then dried over magnesium sulfate and condensed. The obtained residue was purified by silica gel column chromatography (pentane:ether=100:1), to give, as a colorless oil-like substance, 0.089 g of 6-methyl-4,6-dihydrothieno[2,3c]furan (compound (m), 32% yield). The physical properties of the compound are shown below:

$^1$H NMR (CDCl$_3$, 400 MHz, δ ppm) 7.28 (d, J=5.2 Hz, 1H), 6.78 (d, J=5.2 Hz, 1H), 5.40 (m, J=4, 2.8, 6 Hz, 1H), 5.02 (dd, J=4, 7.2 Hz, 1H), 4.92 (dd, J=2.8, 7.2 Hz, 1H), 1.50 (d, J=6 Hz, 3H);

$^{13}$C NMR (CDCl$_3$, 100 MHz) δ ppm 143.28, 142.96, 129.68, 119.18, 77.77, 70.01, 22.91;

MS (m/e) 140 (M$^+$);

IR (neat) ($_{max}$2976, 2864, 2247, 1655, 1446, 1342, 1224, 1095, 1059, 976, 910, 839, 731 cm$^{-1}$.

(B) Synthesis of 6-ethyl-4,6-dihydrothieno[2,3c]furan

In place of 1-[3-(hydroxymethyl)-2-thienyl]-1-ethanone [2-acetyl-thiophene-3-methanol (compound (d))], the 1-[3-(hydroxymethyl)-2-thienyl]-1-propanone (compound (g)) obtained in Example 3(3) was used as a starting material, and the reduction (1) and cyclization (2) were performed according to the above-described method.

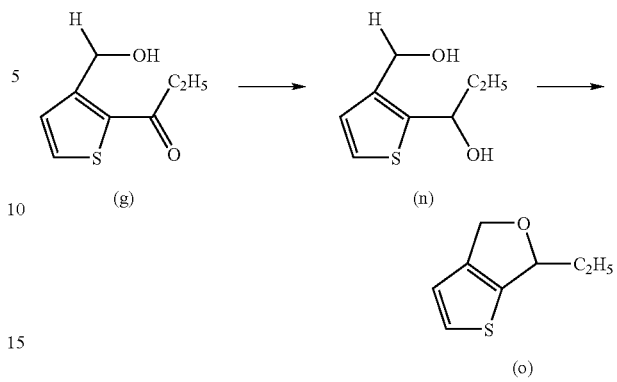

Example 6

Synthesis of 4-methyl-6-ethyl-2,3-dihydrothieno[2,3c]furan 4-methyl-6-ethyl-2,3-dihydrothieno[2,3c]furan (compound (E)) was produced from thiophene-3-carboxaldehyde (compound (A)) according to the following scheme. In the formula, THP represents a tetrahydropyranyl group.

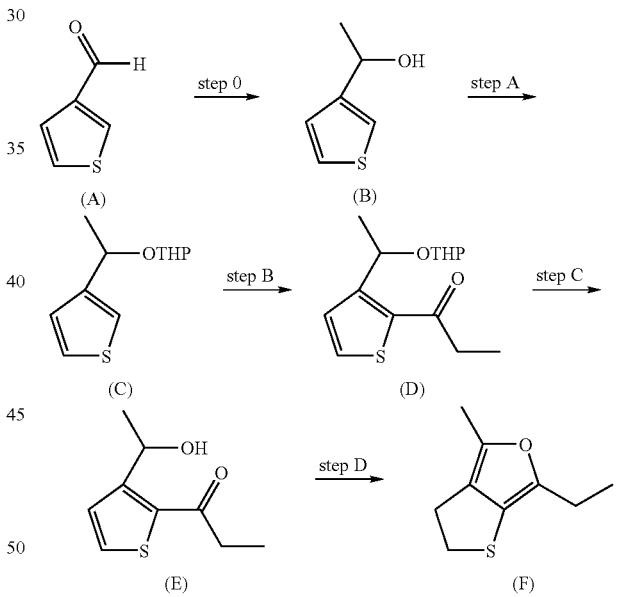

(1) Step 0: Grignard reaction

Synthesis of 3-(1-hydroxyethyl)thiophene (Compound (B))

To 150 ml of THF solution containing 5.0 g (44.58 mmol) of thiophene-3-carboxaldehyde (compound (A)), 16.35 ml (49.04 mmol) of 3M THF solution of methyl magnesium bromide was added dropwise while cooling at 0° C. The solution was returned to room temperature and further stirred for 2 hours. After adding 30 ml of diethylether, the solution was successively washed with a saturated ammonium chloride solution and a saturated sodium chloride solution, and dried over anhydrous magnesium sulfate. Thereafter, the solvent was distilled off under reduced pressure. The obtained residue was purified by silica gel column chromatography (hexane:ethyl acetate=3:1), to yield, as a colorless oil-like substance, 5.30 g of 3-(1-hydroxyethyl)thiophene (compound (B), 99% yield). The physical properties of the compound are shown below:

$^1$H NMR (CDCl$_3$, 600 MHz, (ppm): 7.29 (dd, J=4.8, 2.8 Hz, 1H), 7.18 (d, J=2.8 Hz, 1H), 7.09 (d, J=4.8 Hz, 1H), 4.95 (q, J=6.2 Hz, 1H), 1.96 (brd, 1H), 1.51 (d, J=6.2 Hz, 3H); $^{13}$C NMR (CDCl$_3$, 150 MHz, (ppm) 147.41, 126.24, 125.74, 120.26, 66.62, 24.55.

(2) Step A: Protection of the hydroxy group of 3-(1-hydroxyethyl)thiophene

Synthesis of
2-(3-thienylethyl-1-oxy)tetrahydro-2H-pyrane
(Compound C)

To 6.3 g (49.15 mmol) of the above-obtained 3-(1-hydroxyethyl)thiophene (compound (B)), 50 ml of 3,4-dihydro-2H-pyrane and 0.3 g (1.2 mmol) of p-toluenesulfonic acid were added. After stirring this mixed liquid for 30 minutes at room temperature and adding 100 ml of diethylether, the solution was successively washed with an aqueous saturated sodium hydrogencarbonate solution and a saturated sodium chloride solution, and dried over an anhydrous magnesium sulfate. Thereafter, the solvent was distilled off under reduced pressure. The obtained residue was purified by silica gel column chromatography (hexane:ethyl acetate=30:1), to yield, as a colorless oil-like substance, 2-(3-thienylethyl-1-oxy)tetrahydro-2H-pyrane in which the hydroxy group of 3-(1-hydroxyethyl)thiophene was protected (compound (C), 9.5 g, 91% yield). The physical properties of 2-(3-thienyl-ethyl-1-oxy)tetrahydro-2H-pyrane are shown below:

$^1$H NMR (CDCl$_3$, 600 MHz, (ppm): 7.27 (dd, J=4.8, 2.8 Hz, 1H), 7.14 (d, J=2.8 Hz, 1H), 7.05 (d, J=4.8 Hz, 1H), 4.95 (q, J=6.9 Hz, 1H), 4.44 (m, 1H), 3.92 (m, 1H), 3.48 (m, 1H), 1.85 (m, 1H), 1.64 (m, 1H), 1.49 (d, J=6.9 Hz, 3H), 1.56-1.44 (m, 4H); $^{13}$C NMR (CDCl$_3$, 150 MHz, (ppm) 144.88, 126.02, 125.99, 121.58, 96.09, 69.27, 62.75, 30.89, 25.60, 23.57, 19.89;

$^1$H NMR (CDCl$_3$, 600 MHz, (ppm): 7.25 (dd, J=4.9, 2.8 Hz, 1H), 7.21 (d, J=2.8 Hz, 1H), 7.11 (d, J=2.8 Hz, 1H), 4.92 (q, J=6.9 Hz, 1H), 4.85 (t, J=3.4 Hz, 1H), 3.78 (m, 1H), 3.44 (m, 1H), 1.85 (m, 1H), 1.73 (m, 1H), 1.63 (m, 1H), 1.56-1.44 (m, 3H), 1.46 (d, J=6.9 Hz, 3H); $^{13}$C NMR (CDCl$_3$, 150 MHz, (ppm) 145.65, 126.46, 125.51, 120.49, 96.09, 69.36, 62.25, 30.99, 25.60, 20.92, 19.47.

(3) Step B: Acylation

Synthesis of 1-[3-[1-(tetrahydro-2H-2-pyranyloxy) ethyl]-2-thienyl]-1-propanone (Compound (D))

Into 300 ml of tetrahydrofuran (THF) solution was dissolved 4.0 g (18.84 mmol) of the 2-(3-thienylethyl-1-oxy) tetrahydro-2H-pyrane (compound (C)) obtained in step A. To the resulting mixture, 17.28 ml (1.2M hexane solution, 20.73 mmol) of sec-butyllithium was added dropwise under an argon atmosphere while cooling at −78° C. One hour later, 3.06 g (23.55 mmol) of propionic anhydride was added to the solution, followed by stirring for 30 minutes. Then the solution was returned to room temperature, and further stirred for 1 hour. Subsequently, the solution was washed with an aqueous saturated sodium chloride solution, and the organic layer was dried over anhydrous magnesium sulfate. Thereafter, the solvent was distilled off under reduced pressure. The obtained residue was purified by silica gel column chromatography (hexane:ethyl acetate=50:1), to yield, as a colorless oil-like substance, 1-[3-[1-(tetrahydro-2H-2-pyranyloxy)ethyl]-2-thienyl]-1-propanone (compound (D), 2.1 g, 43% yield). The physical properties of 1-[3-[1-(tetrahydro-2H-2-pyranyloxy) ethyl]-2-thienyl]-1-propanone are shown below:

$^1$H NMR (CDCl$_3$, 600 MHz, (ppm): 7.40 (d, J=5.5 Hz, 1H), 7.25 (d, J=6.2 Hz, 1H), 5.69 (q, J=6.9 Hz, 1H), 4.40 (dd, J=4.7, 2.8 Hz, 1H), 3.91 (m, 1H), 3.46 (m, 1H), 2.87 (q, J=7.6 Hz, 2H), 1.87-1.42 (m, 6H), 1.45 (d, J=6.9 Hz, 3H), 1.18 (t, J=6.9 Hz, 3H); $^{13}$C NMR (CDCl$_3$, 150 MHz, ppm) 193.94, 153.11, 135.31, 129.78, 128.40, 96.81, 69.42, 62.62, 30.91, 25.53, 22.94, 19.77, 14.28, 8.39;

$^1$H NMR (CDCl$_3$, 600 MHz, (ppm): 7.38 (d, J=4.8 Hz, 1H) 7.25 (d, J=6.2 Hz, 1H), 5.60 (q, J=6.2 Hz, 1H), 4.75 (dd, J=4.7, 2.8 Hz, 1H), 3.63 (m, 1H), 3.32 (m, 1H), 2.87 (q, J=7.6 Hz, 2H), 1.87-1.42 (m, 6H), 1.39 (d, J=6.2 Hz, 3H), 1.24 (t, J=6.9 Hz, 3H); $^{13}$C NMR (CDCl$_3$, 150 MHz, (ppm) 194.01, 153.59, 133.40, 129.42, 129.10, 97.83, 70.55, 62.87, 31.17, 25.46, 21.96, 19.98, 14.21, 8.44.

(4) Step C: Deprotection

Synthesis of 1-[3-(1-hydroxyethyl)-2-thienyl]-1-propanone (Compound (E))

Into methanol was dissolved 2.1 g (7.83 mmol) of the 1-[3-[1-(tetrahydro-2H-2-pyranyloxy)ethyl]-2-thienyl]-1-propanone (Compound (D)) prepared in step B, and camphor sulfonic acid was added to 150 ml of the solution at room temperature while stirring. After stirring for 15 minutes, 1.08 g (7.83 mmol) of sodium carbonate was added to terminate the reaction. After filtering the reaction solution, the filtrate was distilled off under reduced pressure. The obtained residue was purified by silica gel column chromatography (hexane: ethyl acetate=3:1), to yield, as a colorless oil-like substance, 1-[3-(1-hydroxyethyl)-2-thienyl]-1-propanone (compound (E), 1.27 g, 88% yield). The physical properties of the 1-[3-(1-hydroxyethyl)-2-thienyl]-1-propanone are shown below:

$^1$H NMR (CDCl$_3$, 600 MHz, ppm); 7.49 (d, J=5.5 Hz, 1H) 7.19 (d, J=5.5 Hz, 1H), 5.14 (m, 1H), 2.82 (q, J=6.9 Hz, 2H), 1.53 (d, J=6.2 Hz, 3H), 1.24 (t, J=6.9 Hz, 3H);

$^{13}$C NMR (CDCl$_3$, 150 MHz, ppm) 193.61, 154.21, 134.60, 130.16, 129.16, 65.21, 30.40, 22.30, 21.18.

(5) Step D: Reduction with Cyclization

Synthesis of
4-methyl-6-ethyl-2,3-dihydrothieno[2,3c]furan
(Compound (F))

Compound (E) (1.27 g (6.90 mmol)) prepared in the above step C was dissolved in 20 ml of toluene solution. Subsequently, to the resulting mixture, 92 mg (0.16 mmol) of tris (triphenylphosphine)rhodium (I) chloride was added. The solution was stirred while heating at 100° C. for 24 hours under 1 Mpa hydrogen atmosphere. The solution was condensed, and then the obtained residue was purified by silica gel column chromatography (pentane:diethylether=100:1), to yield, as a colorless oil-like substance, 670 mg of 4-methyl-6-ethyl-2,3-dihydrothieno[2,3c]furan (compound (F), 58% yield). The physical properties of the 4-methyl-6-ethyl-2,3-dihydrothieno[2,3c]furan are shown below:

$^1$H NMR (CDCl$_3$, 600 MHz, (ppm): 3.57 (t, J=6.9 Hz, 2H), 2.74 (t, J=6.9 Hz, 2H), 2.53 (q, J=7.6 Hz, 2H), 2.15 (s, 3H), 1.19 (t, J=7.6 Hz, 3H);

$^{13}$C NMR (CDCl$_3$, 150 MHz, (ppm): 143.56, 140.48, 126.81, 120.92, 42.04, 25.23, 20.96, 12.75, 12.01.

Example 7

Synthesis of 4-methyl-2,3-dihydrothieno[2,3c]furan

According to the following scheme, 4-methyl-2,3-dihydrothieno[2,3c]furan was synthesized.

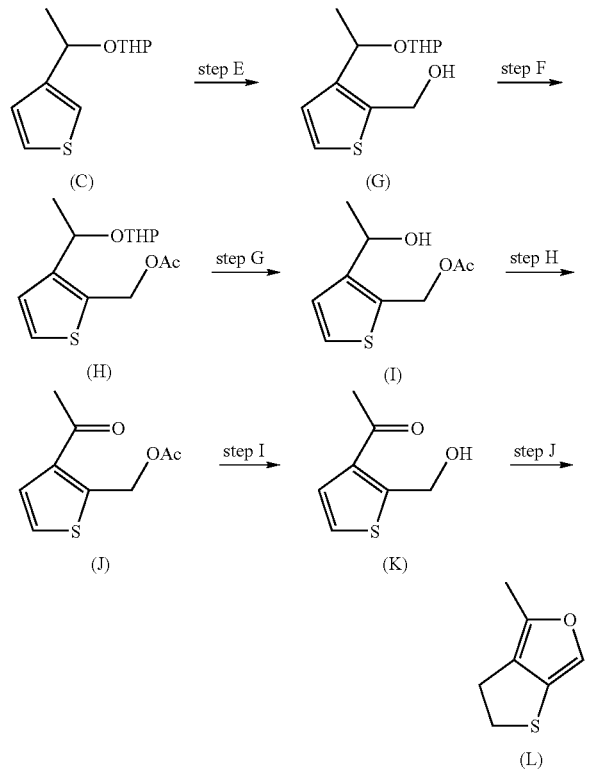

(1) Step F: Hydroxymethylation

Synthesis of 1-[3-[1-(tetrahydro-2H-2-pyranyloxy) ethyl]-2-thienyl]-1-methanol (compound (G))

To 40 ml of THF solution of 500 mg (2.36 mmol) of 2-(3-thienylethyl-1-oxy)tetrahydro-2H-pyrane, 2.93 ml (1.2 M hexane solution, 3.52 mmol) of sec-butyllithium was added dropwise while stirring at −78° C. One hour later, 225 mg (7.04 mmol) of paraformaldehyde was added to the solution, and stirred for 30 minutes. Then, the resulting mixture was returned to room temperature, and further stirred for 1 hour. Subsequently, the solution was washed with a saturated sodium chloride solution, and the organic layer was dried over anhydrous magnesium sulfate. Thereafter, the solvent was distilled off under reduced pressure. The obtained residue was purified by silica gel column chromatography (hexane: ethyl acetate=5:1), to yield, as a colorless oil-like substance, 301 mg of 1-[3-[1-(tetrahydro-2H-2-pyranyloxy)ethyl]-2-thienyl]-1-methanol (compound (G), 53% yield). The physical properties of 1-[3-[1-(tetrahydro-2H-2-pyranyloxy) ethyl]-2-thienyl]-1-methanol are shown below:

$^1$H NMR (CDCl$_3$, 600 MHz, (ppm): 7.20 (d, J=4.8 Hz, 1H), 7.00 (d, J=4.8 Hz, 1H), 4.93 (q, J=6.9 Hz, 1H), 4.76 (d, J=13.2 Hz, 1H), 4.75 (d, J=13.2 Hz, 1H), 4.44 (m, 1H), 3.92 (m, 1H), 3.48 (m, 1H), 1.83-1.49 (m, 6H), 1.46 (d, J=6.9 Hz, 3H); $^{13}$C NMR (CDCl$_3$, 150 MHz), (ppm) 155.28, 129.69, 125.28, 123.68, 97.33, 64.43, 62.82, 62.39, 30.83, 25.79, 23.67, 19.41

$^1$H NMR (CDCl$_3$, 600 MHz, (ppm): 7.22 (d, J=4.8 Hz, 1H), 6.99 (d, J=4.8 Hz, 1H), 4.95 (q, J=6.9 Hz, 1H), 4.79 (d, J=13.2 Hz, 1H), 4.81 (d, J=13.2 Hz, 1H), 4.40 (m, 1H), 3.90 (m, 1H), 3.43 (m, 1H), 1.83-1.49 (m, 6H), 1.40 (d, J=6.9 Hz, 3H); $^{13}$C NMR (CDCl$_3$, 150 MHz), (ppm) 155.01, 129.99, 124.96, 123.03, 98.01, 64.68, 62.79, 62.55, 30.32, 25.50, 23.63, 19.87.

(2) Step G: Acetylation

Synthesis of 3-[1-(tetrahydro-2H-2-pyranyloxy) ethyl]-2-thenyl acetate (Compound (H))

263 mg (2.58 mmol) of acetic anhydride was added to 6.0 ml of the pyridine solution of 500 mg (2.06 mmol) of 1-[3-[1-(tetrahydro-2H-2-pyranyloxy)ethyl]-2-thienyl]-1-methanol prepared in step F. After stirring for 2 hours at room temperature, 20 ml of diethylether was added, and an aqueous saturated potassium-hydrogen sulfate solution was further added to the solution. The organic layer was washed with a saturated sodium chloride solution, and dried over magnesium sulfate. Then, the solvent was distilled off under reduced pressure. The obtained residue was purified by silica gel column chromatography (hexane:ethyl acetate=10:1), to yield, as a colorless oil-like substance, 0.62 g of 3-[1-(tetrahydro-2H-2-pyranyloxy)ethyl]-2-thenyl acetate (compound (H), 98% yield). The physical properties of the compound are shown below:

$^1$H NMR (CDCl$_3$, 600 MHz, (ppm): 7.21 (d, J=4.8 Hz, 1H), 7.01 (d, J=4.8 Hz, 1H), 5.34 (d, J=13.2 Hz, 1H), 5.23 (d, J=13.2 Hz, 1H), 4.95 (q, J=6.9 Hz, 1H), 4.40 (m, 1H), 3.89 (m, 1H), 3.40 (m, 1H), 2.87 (s, 3H) 1.83-1.49 (m, 6H), 1.46 (d, J=6.9 Hz, 3H); $^{13}$C NMR (CDCl$_3$, 150 MHz, (ppm) 174.56, 143.41, 128.67, 123.29, 122.52, 97.33, 64.63, 62.82, 61.78, 31.97, 25.11, 24.69, 21.32, 19.76

$^1$H NMR (CDCl$_3$, 600 MHz, (ppm): 7.23 (d, J=4.8 Hz, 1H), 6.98 (d, J=4.8 Hz, 1H), 5.33 (d, J=13.2 Hz, 1H), 5.20 (d, J=13.2 Hz, 1H), 4.91 (q, J=6.9 Hz, 1H), 4.37 (m, 1H), 3.86 (m, 1H), 3.44 (m, 1H), 2.84 (s, 3H) 1.83-1.49 (m, 6H), 1.41 (d, J=6.9 Hz, 3H); $^{13}$C NMR (CDCl$_3$, 150 MHz, (ppm) 174.22, 142.99, 128.48, 123.78, 122.46, 97.31, 64.78, 62.77, 61.65, 32.10, 24.96, 24.73, 21.46, 19.78.

(3) Step H: Deprotection of a THP Group

Synthesis of 1-[2-[1-acetoxymethyl]-3-thienyl]-1-ethanol (Compound (I))

Into methanol, the 3-[1-(tetrahydro-2H-2-pyranyloxy) ethyl]-2-thenyl acetate (compound (H), 498 mg (1.75 mmol)) prepared in step G was dissolved. To 40 ml of the solution, camphor sulfonic acid was added at room temperature while stirring. After stirring for 15 minutes, the solution was distilled off under reduced pressure. Then, 20 ml of diethylether was added to the obtained residue, and an aqueous saturated sodium hydrogen carbonate solution was further added for extraction. The organic layer was washed with a saturated sodium chloride solution, and dried over magnesium sulfate. Then, the solvent was distilled off under reduced pressure. The obtained residue was purified by silica gel column chromatography (hexane:ethyl acetate=3:1), to prepare 250 mg of 1-[2-[1-acetoxymethyl]-3-thienyl]-1-ethanol (compound (I), 71% yield). The physical properties of the 1-[2-[1-acetoxymethyl]-3-thienyl]-1-ethanol are shown below:

$^1$H NMR (CDCl$_3$, 600 MHz, (ppm): 7.26 (d, J=4.8 Hz, 1H), 7.08 (d, J=4.8 Hz, 1H), 5.36 (d, J=13.6 Hz, 1H), 5.21 (d, J=13.6 Hz, 1H), 5.11 (q, J=6.2 Hz, 1H), 2.41 (brd, 1H), 2.06 (s, 3H), 1.50 (d, J=6.2 Hz, 3H);

$^{13}$C NMR (CDCl$_3$, 100 MHz, (ppm) 171.02, 145.57, 132.35, 126.13, 126.07, 64.30, 58.40, 24.11, 21.09.

(4) Step I: Oxidation of a Hydroxy Group

Synthesis of 1-[2-[1-acetoxymethyl]-3-thienyl]-1-ethanone (compound (J))

To 15 ml of dichloromethane solution of 1-[2-[1-acetoxymethyl]-3-thienyl]-1-ethanol (compound (I), 250 mg (1.25 mmol)), 1.18 g (14.98 mmol) of pyridine, and 0.748 g (7.49 mmol) of chrome oxide (VI) were added, and stirred for 15 minutes. Then, the 1-[2-[1-acetoxymethyl]-3-thienyl]-1-ethanol prepared in step H was added, and stirred for 10 minutes. The solution was filtered, neutralized with dilute hydrochloric acid, and extracted with dichloromethane. The organic layer was washed with a saturated sodium chloride solution, and dried over magnesium sulfate. Then, the solvent was distilled off under reduced pressure. The obtained organic layer was washed with a saturated sodium chloride solution, and dried over magnesium sulfate. Then, the solvent was distilled off under reduced pressure. The obtained residue was purified by silica gel column chromatography (hexane:ethyl acetate=3:1), to prepare 225 mg of 1-[2-[1-acetoxymethyl]-3-thienyl]-1-ethanone (compound (J), 91% yield). The physical properties of the 1-[2-[1-acetoxymethyl]-3-thienyl]-1-ethanone are shown below:

$^1$H NMR (CDCl$_3$, 600 MHz, (ppm): 7.38 (d, J=5.5 Hz, 1H), 7.21 (d, J=5.5 Hz, 1H), 5.60 (s, 2H), 2.51 (s, 3H), 2.13 (s, 3H);

$^{13}$C NMR (CDCl$_3$, 150 MHz, (ppm) 193.74, 170.33, 148.20, 136.40, 128.78, 123.98, 62.01, 29.47, 20.87.

(5) Step J: Deprotection of an Acetyl Group

Synthesis of 1-[2-(hydroxymethyl)-3-thienyl]-1-ethanone (Compound (K))

To 35 ml of methanol solution of 735 mg (3.71 mmol) of the 1-[2-[1-acetoxymethyl]-3-thienyl]-1-ethanone prepared in step I, 3.5 ml of aqueous 2N-sodium hydroxide solution was added, followed by stirring for 15 minutes. To the solution, 100 ml of diethylether was added, and the resulting mixture was neutralized with dilute hydrochloric acid. The organic layer was dried over magnesium sulfate, and the solvent was distilled off under reduced pressure. The obtained residue was purified by silica gel column chromatography (hexane:ethyl acetate=3:1), to yield 470 mg of 1-[2-hydroxymethyl]-3-thienyl]-1-ethanone (compound (K), 81% yield). The physical properties of the 1-[2-(hydroxymethyl)-3-thienyl]-1-ethanone are shown below:

$^1$H NMR (CDCl$_3$, 600 MHz, (ppm): 7.42 (d, J=5.5 Hz, 1H), 7.17 (d, J=5.5 Hz, 1H), 4.83 (s, 2H), 2.56 (s, 3H);

$^{13}$C NMR (CDCl$_3$, 150 MHz, (ppm) 195.68, 153.00, 137.09, 129.54, 123.26, 59.10, 29.42.

(6) Step K: Reduction and Cyclization

Synthesis of 4-methyl-2,3-dihydrothieno[2,3c]furan (Compound (L))

The compound (K) (580 mg (3.71 mmol)) prepared in the above step J was dissolved in 20 ml of toluene solution. Subsequently, 343 mg (0.371 mmol) of tris(triphenylphosphine)rhodium (I) chloride was added thereto. The solution was stirred at 100° C. for 32 hours under a 1 Mpa hydrogen atmosphere. The residue obtained by condensing the solution was purified by silica gel column chromatography (pentane:diethyl ether=100:1), to yield, as a colorless oil-like substance, 236 mg of 4-methyl-2,3-dihydrothieno[2,3c]furan (compound (L), 44% yield). The physical properties of the 4-methyl-2,3-dihydrothieno[2,3c]furan are shown below:

$^1$H NMR (CDCl$_3$, 600 MHz, (ppm): 6.88 (s, 1H), 3.63 (t, J=6.9 Hz, 2H), 2.79 (t, J=6.9 Hz, 2H), 2.19 (s, 3H);

$^{13}$C NMR (CDCl$_3$, 150 MHz, (ppm) 142.89, 129.84, 128.55, 126.75, 42.17, 25.09, 12.82.

Example 8

Synthesis of 4-ethyl-2,3-dihydrothieno[2,3c]furan

According to the following scheme, 4-ethyl-2,3-dihydrothieno[2,3c]furan (compound (T)) was prepared from thiophene-3-carboxaldehyde (compound (A)).

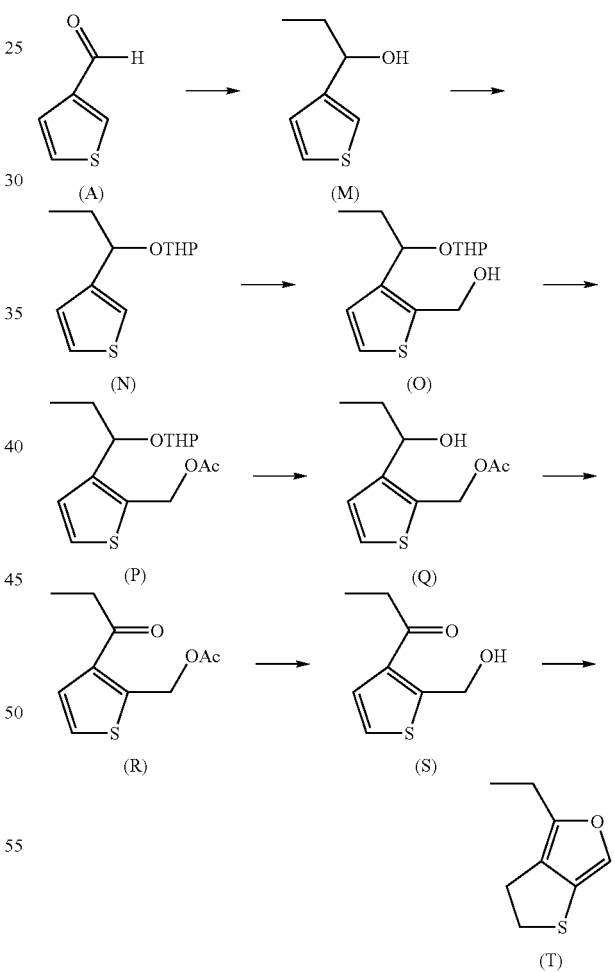

(1) Synthesis of 3-(1-hydroxypropyl)thiophene (Compound (M))

According to step A of Example 6, 12.45 g of 3-(1-hydroxypropyl)thiophene (compound (M), 98% yield) was prepared from 10.0 g (89.17 mmol) of thiophene-3-carboxaldehyde (compound (A)). The physical properties of the 3-(1-hydroxypropyl)thiophene are shown below:

$^1$H NMR (CDCl$_3$, 600 MHz, (ppm): 7.29 (dd, J=4.8, 2.8 Hz, 1H), 7.17 (d, J=2.8 Hz, 1H), 7.06 (d, J=4.8 Hz, 1H), 4.68 (t, J=6.2 Hz, 1H), 1.92 (brd, 1H), 1.80 (qd, J=7.6, 6.2 Hz, 2H), 0.92 (t, J=6.2 Hz, 3H);

$^{13}$C NMR (CDCl$_3$, 150 MHz, (ppm) 146.22, 126.11, 125.77, 120.84, 72.11, 31.34, 10.11.

(2) Synthesis of 2-(3-thienylpropyl-1-oxy)tetrahydro-2H-pyrane (Compound (N))

According to step B of Example 6, 17.89 g of 2-(3-thienylethyl-1-oxy)tetrahydro-2H-pyrane (compound (N), 90% yield) was prepared from 10.0 g (89.17 mmol) of 3-(1-hydroxypropyl)thiophene (compound (M)). The physical properties of the 2-(3-thienylethyl-1-oxy)tetrahydro-2H-pyrane are shown below:

$^1$H NMR (CDCl$_3$, 600 MHz, (ppm): (7.27 (dd, J=4.8, 2.8 Hz), 7.25 (dd, J=5.5, 3.4 Hz), 1H (7.18 (d, J=3.4 Hz), 7.13 (d, J=1.7 Hz), 1H), (7.08 (d, J=4.8 Hz), 7.03 (d, J=4.8 Hz), 1H), (4.81 (t, J=3.7 Hz), 4.69 (t, J=7.0 Hz), 1H), 4.65 (t, J=6.2 Hz), 4.44 (t, J=3.7 Hz), 1H) (3.93 (m), 3.65 (m), 1H), (3.49 (m), 3.35 (m), 1H), 1.91-1.44 (m, 8H), (0.91 (t, J=7.6 Hz), 0.84 (t, J=7.6 Hz), 3H);

$^{13}$C NMR (CDCl$_3$, 150 MHz, (ppm) (144.46, 143.65), (126.49, 126.18) (125.86, 125.25) (123.00, 121.00) (97.72, 95.26) (75.92, 74.49), (62.43, 62.19), (30.84, 30.82), (30.42, 28.76), (25.65, 25.56), (19.68, 19.43), (10.54, 9.65).

(3) Synthesis of 1-[3-[1-(tetrahydro-2H-2-pyranyloxy)propyl-2-thienyl]-1-methanol (compound (O))

According to step F of Example 7, 3.99 g of 1-[3-[1-(tetrahydro-2H-2-pyranyloxy)propyl]-2-thienyl]-1-methanol (compound (O), 46% yield) was prepared from 7.70 g (18.84 mmol) of 2-(3-thienylethyl-1-oxy)tetrahydro-2H-pyrane (compound (N)). The physical properties of the compound are shown below:

$^1$H NMR (CDCl$_3$, 600 MHz, (ppm): (7.22 (d, J=4.8 Hz), 7.20 (d, J=4.8 Hz), 1H), (7.03 (d, J=4.8 Hz), 7.00 (d, J=4.8 Hz), 1H), 4.96 (m, 1H), 4.74 (m, 1H), 4.72 (m, 1H), 4.40 (m, 1H), 3.90 (m, 1H), 3.45 (m, 1H), 1.87-1.47 (m, 6H), 0.98 (m, 2H) (0.89 (t, J=6.9 Hz), 0.84 (t, J=6.9 Hz), 3H);

$^{13}$C NMR (CDCl$_3$, 150 MHz, (ppm) (155.28, 155.02), (129.69, 129.44) (125.28, 125.01), (123.68, 123.55) (97.33, 96.98), (64.43, 64.39) (62.82, 62.55) (62.39, 62.11) (30.83, 30.57) (25.79, 25.66) (23.67, 23.60) (19.41, 19.02) (10.23, 10.09).

(4) Synthesis of 1-[3-[1-(tetrahydro-2H-2-pyranyloxy)propyl]-2-thienyl]-1-hydroxymethyl acetate (compound (P))

4.55 g of 3-[1-(tetrahydro-2H-2-pyranyloxy)ethyl]-2-thenyl acetate (compound (P), 97% yield) was prepared from 3.99 g (16.60 mmol) of 1-[3-[1-(tetrahydro-2H-2-pyranyloxy)propyl]-2-thienyl]-1-methanol (compound (O)). The physical properties of the compound (P) are shown below:

$^1$H NMR (CDCl$_3$, 600 MHz, (ppm): 7.40 (d, J=5.5 Hz), 7.37 (d, J=5.5 Hz), 1H), 7.25 (d, J=6.2 Hz), 7.22 (d, J=6.2 Hz), 1H), 5.69 (m, 1H), 4.75 (m, 1H), 4.56 (m, 1H), 4.23 (m, 1H), 3.91 (m, 1H), 3.46 (m, 1H), (2.87 (s), 2.85 (s), 3H), 1.87-1.42 (m, 6H), 1.45 (m, 2H), 1.18 (t, J=6.9 Hz), 1.16 (t, J=6.9 Hz), 3H);

$^{13}$C NMR; (CDCl$_3$, 150 MHz, (ppm) 193.94, 153.11, 135.31, 129.78, 128.40, 96.81, 69.42, 62.62, 59.33, 30.91, 25.53, 22.94, 19.77, 14.28, 8.39.

(5) Synthesis of 1-[2-[1-acetoxymethyl]-3-thienyl]-1-propanol (Compound (Q))

According to step H of Example 7, 2.66 g of 1-[2-[1-acetoxymethyl]-3-thienyl]-1-propanol (compound (Q), 77% yield) was prepared from 4.55 g (16.11 mmol) of 3-[1-(tetrahydro-2H-2-pyranyloxy)ethyl]-3-thenyl acetate (compound (P)). The physical properties of the compound (Q) are shown below:

$^1$H NMR (CDCl$_3$, 600 MHz, (ppm): 7.26 (d, J=5.5 Hz, 1H), 7.03 (d, J=5.5 Hz, 1H), 5.34 (d, J=13.1 Hz, 1H), 5.20 (q, J=13.1 Hz, 1H), 4.80 (t, J=6.2 Hz 1H), 2.05 (s, 3H), 1.87-1.73 (m, 2H), 0.90 (t, J=7.6 Hz, 3H); $^{13}$C NMR (CDCl$_3$, 150 MHz, (ppm) 170.98, 144.46, 132.93, 126.30, 126.08, 69.81, 58.41, 30.99, 21.08, 10.33.

(6) Synthesis of 1-[2-[1-acetoxymethyl]-3-thienyl]-1-propanone (Compound (R))

According to step I of Example 7, 2.30 g of 1-[2-[1-acetoxymethyl]-3-thienyl]-1-propanone (compound (R), 87% yield) was prepared from 2.66 g (12.41 mmol) of 1-[2-[1-acetoxymethyl]-3-thienyl]-1-propanol (compound (Q)). The physical properties of the compound (R) are shown below:

$^1$H NMR (CDCl$_3$, 600 MHz, (ppm): 7.38 (d, J=5.5 Hz, 1H), 7.21 (d, J=5.5 Hz, 1H), 5.60 (s, 2H), 2.51 (s, 3H), 2.26 (q, J=6.9 Hz, 2H), 1.09 (t, J=6.9 Hz, 3H);

$^{13}$C NMR (CDCl$_3$, 150 MHz, (ppm) 193.63, 168.63, 149.21, 135.22, 126.50, 123.20, 61.78, 28.40, 20.45, 14.69.

(7) Synthesis of 1-[2-(hydroxymethyl)-3-thienyl]-1-propanone (Compound (S))

According to step J of Example 7, 1.60 g of 1-[2-(hydroxymethyl)-3-thienyl]-1-propanone (compound (S), 87% yield) was prepared from 2.30 g (10.84 mmol) of 1-[2-[1-acetoxymethyl]-3-thienyl]-1-propanone (compound (R)). The physical properties of the compound are shown below:

$^1$H NMR (CDCl$_3$, 600 MHz, (ppm): 7.41 (d, J=5.5 Hz, 1H), 7.18 (d, J=5.5 Hz, 1H), 4.83 (s, 2H), 2.56 (q, J=7.6 Hz, 2H), 1.19 (t, J=7.6 Hz, 3H);

$^{13}$C NMR (CDCl$_3$, 150 MHz, (ppm) 196.60, 153.21, 137.33, 129.80, 123.39, 59.12, 29.42, 12.46.

(8) Synthesis of 4-ethyl-2,3-dihydrothieno[2,3c]furan (Compound (T))

According to step K of Example 7, 0.44 g of 4-ethyl-2,3-dihydrothieno[2,3c]furan (compound (T), 30% of yield) was prepared from 1.60 g (9.40 mmol) of 1-[2-(hydroxymethyl)-3-thienyl]-1-propanone (compound (S)). The physical properties of the compound (T) are shown below:

$^1$H NMR (CDCl$_3$, 600 MHz, (ppm): 6.89 (s, 1H), 3.62 (t, J=6.9 Hz, 2H), 2.81 (t, J=6.9 Hz, 2H), 2.50 (q, J=7.6 Hz, 2H), 1.18 (t, J=7.6 Hz, 3H);

$^{13}$C NMR (CDCl$_3$, 150 MHz, (ppm) 144.70, 129.30, 128.81, 127.02, 42.19, 25.09, 12.86, 12.31.

Example 9

Synthesis of 4-ethyl-6-methyl-2,3-dihydrothieno[2,3c]furan

According to the following scheme, 4-ethyl-6-methyl-2,3-dihydrothieno[2,3c]furan (compound (W)) was prepared from 2-(3-thienylpropyl-1-oxy)tetrahydro-2H-pyrane (compound (N)). 2-(3-thienylpropyl-1-oxy)tetrahydro-2H-pyrane (compound (N)) was prepared in steps A and B of Example 6.

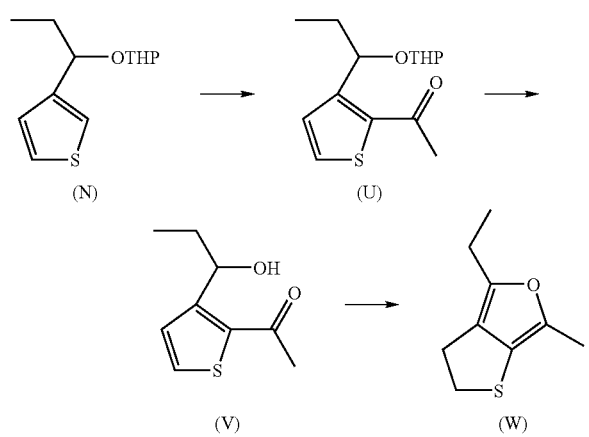

(1) Synthesis of 1-[3-[1-(tetrahydro-2H-2-pyranyloxy)propyl]-2-thienyl]-1-ethanone (Compound (U))

According to step C of Example 6, 2.77 g of 1-[3-[1-(tetrahydro-2H-2-pyranyloxy)propyl]-2-thienyl]-1-ethanone (compound (U), 47% yield) was prepared from 5.00 g (22.09 mmol) of 2-(3-thienylpropyl-1-oxy)tetrahydro-2H-pyrane (compound (N)). The physical properties of the compound (U) are shown below:

$^1$H NMR (CDCl$_3$, 600 MHz, (ppm): (7.41 (d, J=5.5 Hz), 7.39 (d, J=4.8 Hz), 1H), 7.26 (m, 1H), 5.93 (m, 1H), 4.72 (m, 1H), 3.91 (m, 1H), 3.48 (m, 1H) (2.88 (s), 2.86 (s), 3H), 1.89-1.41 (m, 6H), 1.13 (m, 2H), (0.94 (t, J=6.9 Hz) 0.90 (t, J=6.9 Hz), 3H);

$^{13}$C NMR (CDCl$_3$, 150 MHz, (ppm) (195.36, 194.96), (156.54, 151.11), (135.31, 131.46), (130.79, 129.40) (129.26, 128.05), (97.80, 96.03), (70.69, 68.89), (62.99, 62.37) (30.75, 30.10), (25.57, 25.01), (23.58, 20.91), (20.11, 19.60), (14.32, 14.09), (8.41, 8.26).

(2) Synthesis of 1-[3-(1-hydroxypropyl)-2-thienyl]-1-ethanone (Compound (V))

According to step D of Example 1, 1.58 g of 1-[3-(1-hydroxypropyl)-2-thienyl]-1-ethanone (compound (V), 83% yield) was manufactured from 2.77 g (10.32 mmol) of 1-[3-[1-(tetrahydro-2H-2-pyranyloxy)propyl]-2-thienyl]-1-ethanone (compound (U)). The physical properties of the compound (V) are shown below:

$^1$H NMR (CDCl$_3$, 600 MHz, (ppm): 7.48 (d, J=5.5 Hz, 1H), 7.14 (d, J=5.5 Hz, 1H), 4.86 (dd, J=7.6, 2.1 Hz, 1H), 2.58 (s, 3H), 1.85-1.73 (m, 2H), 0.96 (t, J=7.8 Hz, 3H);

$^{13}$C NMR (CDCl$_3$, 150 MHz, (ppm) 192.71, 154.00, 135.78, 131.04, 130.08, 71.52, 29.96, 29.70, 10.74.

(3) Synthesis of 4-ethyl-6-methyl-2,3-dihydrothieno[2,3c]furan (Compound (W))

According to step E of Example 1, 1.08 g of 4-ethyl-6-methyl-2,3-dihydrothieno[2,3c]furan (compound (W), 75% of yield) was manufactured from 1.58 g (8.57 mmol) of 1-[3-(1-hydroxypropyl)-2-thienyl]-1-ethanone (compound (V)). The physical properties of the compound (W) are shown below:

$^1$H NMR (CDCl$_3$, 600 MHz, (ppm): 3.58 (t, J=6.9 Hz, 2H), 2.80 (t, J=6.9 Hz, 2H), 2.52 (q, J=7.6 Hz, 2H), 2.15 (s, 3H), 1.18 (t, J=7.6 Hz, 3H);

$^{13}$C NMR (CDCl$_3$, 150 MHz, (ppm) 145.99, 138.07, 125.75, 122.07, 42.17, 25.83, 21.04, 12.85, 12.26.

Example 10

Synthesis of 4,6-diethyl-2,3-dihydrothieno[2,3c]furan

According to the following scheme, 4,6-diethyl-2,3-dihydrothieno[2,3c]furan (compound (Z)) was manufactured from 2-(3-thienylpropyl-1-oxy)tetrahydro-2H-pyrane (compound (N)).

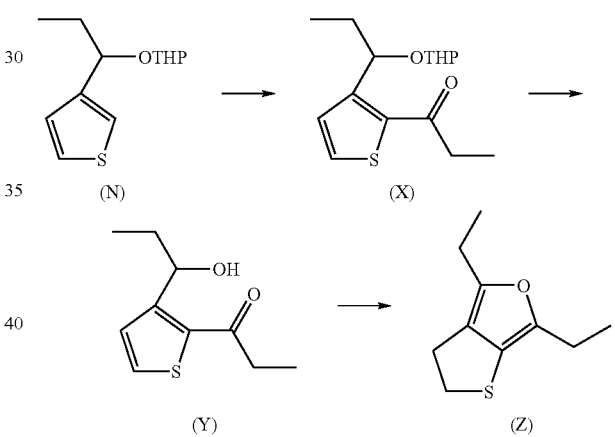

(1) Synthesis of 1-[3-[1-(tetrahydro-2H-2-pyranyloxy)propyl]-2-thienyl]-1-propanone (compound (X))

According to step C of Example 6, 2.95 g of 1-[3-[1-(tetrahydro-2H-2-pyranyloxy)propyl]-2-thienyl]-1-propanone (compound (X), 49% yield) was prepared from 5.00 g (22.09 mmol) of 2-(3-thienylpropyl-1-oxy)tetrahydro-2H-pyrane (compound (N)). The physical properties of the compound (X) are shown below:

$^1$H NMR (CDCl$_3$, 600 MHz, (ppm): (7.41 (d, J=5.5 Hz), 7.39 (d, J=4.8 Hz), 1H), 7.26 (m, 1H), 5.67 (m, 1H), (4.72 (dd, J=4.7, 2.8 Hz), 4.42 (dd, J=4.7, 2.8 Hz), 1H), (3.91 (m), 3.67 (m), 1H), (3.48 (m), 3.31 (m), 1H), 2.86 (m, 3H), 1.89-1.41 (m, 10H), 1.23 (t, J=6.9 Hz), 1.19 (t, J=6.9 Hz), 3H);

$^{13}$C NMR (CDCl$_3$, 150 MHz (ppm) (194.01, 193.94), (153.59, 153.11), (135.31, 133.40), (129.78, 129.42), (129.10, 128.40), (97.83, 96.81) (70.55, 69.42), (62.87, 62.62) (31.17, 30.91), (25.53, 25.46), (22.94, 21.96), (19.98, 19.77), (14.29, 14.26) (10.43, 10.30) (8.44, 8.39).

(2) Synthesis of 1-[3-(1-hydroxypropyl)-2-thienyl]-1-propanone (Compound (Y))

According to step D of Example 6, 1.63 g of 1-[3-(1-hydroxypropyl)-2-thienyl]-1-propanone (compound (Y), 79% yield) was prepared from 2.95 g (10.45 mmol) of 1-[3-[1-(tetrahydro-2H-2-pyranyloxy)propyl]-2-thienyl]-1-propanone (compound (X)). The physical properties of the compound (Y) are shown below:

$^1$H NMR (CDCl$_3$, 600 MHz, (ppm); 7.50 (d, J=5.5 Hz, 1H), 7.20 (d, J=5.5 Hz, 1H), 5.16 (m, 1H), 2.82 (q, J=6.9 Hz, 2H), 1.79 (m, 2H), 0.96 (t, J=6.9 Hz, 3H);

$^{13}$C NMR (CDCl$_3$, 150 MHz, (ppm) 193.86, 155.00, 134.16, 131.53, 129.99, 67.61, 30.62, 22.35, 21.06, 11.74.

(3) Synthesis of 4,6-diethyl-2,3-dihydrothieno[2,3c]furan (Compound (Z))

According to step E of Example 6, 1.38 g of 4,6-diethyl-2,3-dihydrothieno[2,3c]furan (compound (Z), 92% yield) was prepared from 1.63 g (8.22 mmol) of 1-[3-(1-hydroxypropyl)-2-thienyl]-1-propanone (compound (Y)). The physical properties of the compound (Z) are shown below:

$^1$H NMR (CDCl$_3$, 600 MHz, (ppm): 3.58 (t, J=6.9 Hz, 2H), 2.80 (t, J=6.9 Hz, 2H), 2.54 (q, J=7.6 Hz, 2H), 2.53 (q, J=7.6 Hz, 2H), 1.19 (t, J=7.6 Hz, 3H), 1.18 (t, J=7.6 Hz, 3H);

$^{13}$C NMR (CDCl$_3$, 150 MHz, (ppm) 145.78, 143.31, 125.78, 120.98, 42.02, 25.42, 21.04, 20.96, 12.25, 11.95.

Example 11

1 ppm of kahweofuran was added to a coffee flavor composition having the following formulation to prepare coffee flavoring.

| Ingredient | Part by weight |
| --- | --- |
| Vanillin | 1 |
| Cycloten | 5 |
| Maltol | 5 |
| Diacetyl | 1 |
| 5-methyl furfural | 1 |
| Furfuryl alcohol | 10 |
| Furfuryl mercaptan (10% sol) | 2 |
| Furaneol | 5 |
| Coffee extract | 250 |
| Ethanol | 320 |
| Water | 400 |
| Total | 1000 |

Example 12

10 ppm of kahweofuran was added to 100 parts by weight of coffee flavoring obtained by distilling coffee beans. When 0.1 part by weight of the resulting mixture was added to 100 parts by weight of coffee extract obtained from medium roast coffee having an L value of 23, coffee with a stronger roasted aroma was obtained.

Example 13

When 10 ppm of 6-ethyl-2,3-dihydrothieno[2,3c]furan was added to 100 parts by weight of coffee extract obtained from medium roast coffee having an L value of 23, coffee with a sweeter roasted taste was obtained.

The invention claimed is:

1. A method for producing kahweofuran or an analogue thereof represented by Formula (3a), comprising the step of reducing and cyclizing a thiophene compound represented by Formula (2) in the presence of a transition metal catalyst:

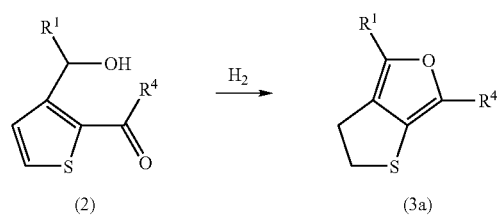

wherein $R^1$ is a hydrogen atom or a $C_1$-$C_4$ lower alkyl group, and $R^4$ is a $C_1$-$C_4$ lower alkyl group.

2. The method according to claim 1, wherein the transition metal catalyst is a rhodium catalyst.

3. The method for producing kahweofuran or an analogue thereof represented by Formula (3a), comprising steps A to D indicated in the scheme given below:

step A: protecting the hydroxy group of compound (4) to produce compound (5);

step B: acylating compound (5) obtained in step A to produce compound (6);

step C: deprotecting compound (6) obtained in step B to produce compound (2); and step D: reducing and cyclizing compound (2) obtained in step C, in the presence of a transition metal catalyst to produce kahweofuran or analogue thereof (3a);

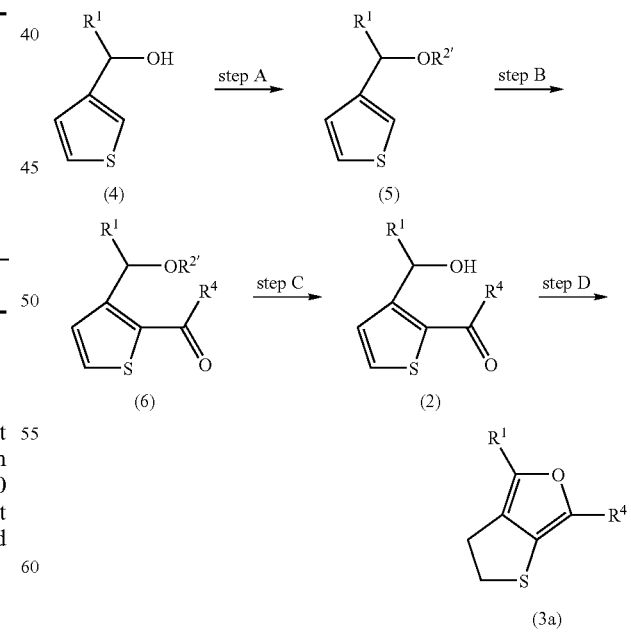

wherein $R^1$ is a hydrogen atom or a $C_1$-$C_4$ lower alkyl group, $R^{2'}$ is an alcohol-protecting group, and $R^4$ is a $C_1$-$C_4$ lower alkyl group.

4. A method for producing thiophene compound (7) comprising the step of cyclizing compound (8) shown in the following scheme:

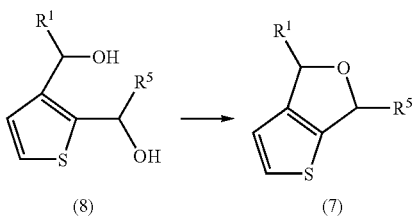

wherein $R^1$ is a hydrogen atom or a $C_1$-$C_4$ lower alkyl group, and $R^5$ is a $C_1$-$C_4$ lower alkyl group.

5. A method for producing kahweofuran or an analogue thereof according to claim 1, wherein $R^1$ is a hydrogen atom.

6. A method for producing kahweofuran or an analogue thereof according to claim 3, wherein $R^1$ is a hydrogen atom.

7. A method for producing a thiophene compound according to claim 4, wherein $R^1$ is a hydrogen atom.

8. A method for producing kahweofuran or an analogue thereof according to claim 1, wherein $R^4$ is a methyl group.

9. A method for producing kahweofuran or an analogue thereof according to claim 3, wherein $R^4$ is a methyl group.

10. A method for producing a thiophene compound according to claim 4, wherein $R^5$ is a methyl group.

11. A method for producing kahweofuran or an analogue thereof according to claim 3, wherein $R^{2'}$ is a tetrahydropyranyl group.

* * * * *